(12) United States Patent
Lassila et al.

(10) Patent No.: US 11,441,139 B2
(45) Date of Patent: Sep. 13, 2022

(54) α-AMYLASE VARIANTS

(71) Applicant: DANISCO US INC., Palo Alto, CA (US)

(72) Inventors: Jonathan K. Lassila, Palo Alto, CA (US); Sandra W. Ramer, Palo Alto, CA (US)

(73) Assignee: DANISCO US INC (157111), Palo Alto, CA (US)

( * ) Notice: Subject to any disclaimer, the term of this patent is extended or adjusted under 35 U.S.C. 154(b) by 0 days.

(21) Appl. No.: 16/639,909

(22) PCT Filed: Aug. 20, 2018

(86) PCT No.: PCT/US2018/047090
§ 371 (c)(1),
(2) Date: Feb. 18, 2020

(87) PCT Pub. No.: WO2019/036721
PCT Pub. Date: Feb. 21, 2019

(65) Prior Publication Data
US 2021/0189363 A1     Jun. 24, 2021

Related U.S. Application Data

(60) Provisional application No. 62/547,425, filed on Aug. 18, 2017, provisional application No. 62/559,179, filed on Sep. 15, 2017.

(51) Int. Cl.
*C12N 9/26*     (2006.01)
*C11D 3/386*     (2006.01)

(52) U.S. Cl.
CPC ............ *C12N 9/2414* (2013.01); *C11D 3/386* (2013.01); *C12Y 302/01001* (2013.01)

(58) Field of Classification Search
None
See application file for complete search history.

(56) References Cited

FOREIGN PATENT DOCUMENTS

WO   WO-2014162001 A1 * 10/2014 ............... C11D 1/29

* cited by examiner

*Primary Examiner* — Richard G Hutson

(57) ABSTRACT

Disclosed are compositions and methods relating to variant alpha-amylases. The variant alpha-amylases are useful, for example, for starch liquefaction and saccharification, for cleaning starchy stains in laundry, dishwashing, and other applications, for textile processing (e.g., desizing), in animal feed for improving digestibility, and for baking and brewing.

3 Claims, 2 Drawing Sheets
Specification includes a Sequence Listing.

```
Amy707-2170D    HHNGTNGTMMQYFEWYLPNDGNHWNRLNSDASNLKSKGITAVWIPPAWKGASQNDVGYGA
Amy707-3915D    -ATVNNGTLMQYFEWYLPNDGQHWNRLNSDASNLKSKGITAVWIPPAYKGTTQNDVGYGA
Amy707          HHNGTNGTMMQYFEWYLPNDGNHWNRLNSDASNLKSKGITAVWIPPAWKGASQNDVGYGA
Amy707-3790H    HHNGTNGTMMQYFEWYLPNDGNHWNRLNSDASNLKSKGITAVWIPPAYKGTSQNDVGYGA
Amy707-3156D    HHNGTNGTLMQYFEWYAPNDGQHWNRLRSDAENLAQKGITAVWIPPAWKGASQNDVGYGA
Amy707-4037D    HHNGTNGTMMQYFEWYLPNDGNHWNRLNSDASNLKSKGITAVWIPPAWKGTSQNDVGYGA
                 .:***:****** ****:*****:***.**  .***********:**::*******

Amy707-2170D    YDLYDLGEFNQKGTVRTKYGTRSQLQAAVTSLKNNGIQVYGDVVMNHKGGADYTETVTAV
Amy707-3915D    YDLYDLGEFNQKGTVRTKYGTRSQLQAAVTSLKNNGIQVYGDAVMNHKGGADATEMVRAV
Amy707          YDLYDLGEFNQKGTVRTKYGTRSQLQAAVTSLKNNGIQVYGDVVMNHKGGADATEMVRAV
Amy707-3790H    YDLYDLGEFNQKGTVRTKYGTRSQLQAAVTSLKNNGIQVYGDVVMNHKGGADATEMVRAV
Amy707-3156D    YDLYDLGEFNQKGTVRTKYGTKAQLKSAVTSLKNNGIQVYGDVVMNHKGGADATETVTAV
Amy707-4037D    YDLYDLGEFNQKGTVRTKYGTRSQLQAAVTSLKNNGIQVYGDVVMNHKGGADATEMVRAV
                *********************::**::***************.********* ** * **

Amy707-2170D    EVNPNNRNQETSGEYNIQAWTRFDFPGRGNTHSSFKWRWYHFDGVDWDQSRRLNNRIYKF
Amy707-3915D    EVNPSNRNQETSGEYNIQAWTGFNFPGRGNTHSSFKWRWYHFDGVDWDQSRRLNNRIYKF
Amy707          EVNPNNRNQEVTGEYTIEAWTRFDFPGRGNTHSSFKWRWYHFDGVDWDQSRRLNNRIYKF
Amy707-3790H    EVNPSNRNQEISGDYTIEAWTKFDFPGRGNTHSSFKWRWYHFDGVDWDQSRRLNNRIYKF
Amy707-3156D    EVNPSNRNQETSGEYNIQAWTRFDFPGRGNTHSSFKWRWYHFDGTDWDQSRRLNNRIYKF
Amy707-4037D    EVNPNNRNQEVTGEYTIEAWTRFDFPGRGNTHSNFKWRWYHFDGVDWDQSRRLNNRIYKF
                ****.***** :*:*.*:*** *:*********.********.****************

Amy707-2170D    --DGKAWDWPVSSENGNYDYLMYADVDFEHPEVVNEMKKWGVWYTNTLGLDGFRIDAVKH
Amy707-3915D    --DGKAWDWPVSSENGNYDYLMYADLDFDHPDVVNEMKEWGVWYANTLGLDGFRIDAVKH
Amy707          RGHGKAWDWEVDTENGNYDYLMYADIDMDHPEVVNELRNWGVWYTNTLGLDGFRIDAVKH
Amy707-3790H    --HGKAWDWPVSSENGNYDYLMYADIDMDHPDVVNELRNWGVWYANTLGLDGFRIDAVKH
Amy707-3156D    --DGKAWDWPVSSENGNYDYLMYADIDMDHPEVVNELRNWGVWYTNTLGLDGFRIDAVKH
Amy707-4037D    --DGKAWDWPVSSENGNYDYLMYADLDFDHPDVANEMKNWGTWYANELNLDGFRLDAVKH
                  .****** *.:*************:*::**:*.**:::**.**:* *.*****:*****

Amy707-2170D    IKYSFTRDWINHVRSATGKNMFAVAEFWKNDLGAIENYLQKTNWNHSVFDVPLHYNLYNA
Amy707-3915D    IKYSFTRDWINHVRSATGKNMFAVAEFWKNDLGAIENYLQKTNWNHSVFDVPLHYNLYNA
Amy707          IKYSFTRDWINHVRSATGKNMFAVAEFWKNDLGAIENYLQKTNWNHSVFDVPLHYNLYNA
Amy707-3790H    IKYSFTRDWINHVRSATGKNMFAVAEFWKNDLGAIENYLQKTNWNHSVFDVPLHYNLYNA
Amy707-3156D    IKYSFTRDWINHVRSATGKNMFAVAEFWKNDLGAIENYLQKTNWNHSVFDVPLHYNLYNA
Amy707-4037D    IDHEYLRDWVNHVRQQTGKNMFAVAEFWKNDLGAIENYLQKTNWNQSVFDAPLHYNLYNA
                *.:.: ***:****.  ********************:*********:****.*********

Amy707-2170D    SKSGGNYDMRNIFNGTVVQRHPSHAVTFVDNHDSQPEEALESFVEEWFKPLAYALTLTRE
Amy707-3915D    SKSGGNYDMRNIFNGTVVQRHPSHAVTFVDNHDSQPEEALESFVEEWFKPLAYALTLTRE
Amy707          SKSGGNYDMRNIFNGTVVQRHPSHAVTFVDNHDSQPEEALESFVEEWFKPLAYALTLTRE
Amy707-3790H    SKSGGNYDMRNIFNGTVVQRHPSHAVTFVDNHDSQPEEALESFVEEWFKPLAYALTLTRE
Amy707-3156D    SKSGGNYDMRNIFNGTVVQRHPSHAVTFVDNHDSQPEEALESFVEEWFKPLAYALTLTRE
Amy707-4037D    SKSGGNYDMRNIFNGTVVQRHPSHAVTFVDNHDSQPEEALESFVEEWFKPLAYALTLTRE
                ************************************************************

Amy707-2170D    QGYPSVFYGDYYGIPTHGVPAMRSKIDPILEARQKYAYGKQNDYLDHHNIIGWTREGNTA
Amy707-3915D    QGYPSVFYGDYYGIPTHGVPAMRSKIDPILEARQKYAYGKQNDYLDHHNIIGWTREGNTA
Amy707          QGYPSVFYGDYYGIPTHGVPAMRSKIDPILEARQKYAYGKQNDYLDHHNIIGWTREGNTA
Amy707-3790H    QGYPSVFYGDYYGIPTHGVPAMRSKIDPILEARQKYAYGKQNDYLDHHNIIGWTREGNTA
Amy707-3156D    QGYPSVFYGDYYGIPTHGVPAMRSKIDPILEARQKYAYGKQNDYLDHHNIIGWTREGDST
Amy707-4037D    QGYPSVFYGDYYGIPTHGVPAMRSKIDPILEARQKYAYGKQNDYLDHHNIIGWTREGDST
                *********************************************************:::
```

```
Amy707-2170D     HPNSGLATLISDGPGGSKWMFVGRNKAGQVWSDITGNRTGTVTINADGWGNFSVNGGSVS
Amy707-3915D     HPNSGLATIMSDGPGGSKWMFVGRNKAGQVWSDITGNRTGTVTINADGWGNFSVNGGSVS
Amy707           HPNSGLATIMSDGAGGSKWMFVGRNKAGQVWSDITGNRTGTVTINADGWGNFSVNGGSVS
Amy707-3790H     HPNSGLATIMSDGAGGSKWMNVGKNNAGEVWYDITGNRTGTVTINADGWGQFHVNGGSVS
Amy707-3156D     KANSGLATIMSDGPGGSKWMNVGKNNAGQVWSDITGNRTGTVTINADGWGQFFVNGGSVS
Amy707-4037D     KANSGLATIMSDGPGGSKWMNVGKQNAGEVWYDITGNRTGTVTINSDGWGQFFVNGGSVS
                 :.******::***.****** **:::**:** **************:****:* ******

Amy707-2170D     IWVNK (SEQ ID NO: 3)
Amy707-3915D     IWVNK (SEQ ID NO: 6)
Amy707           IWVNK (SEQ ID NO: 1)
Amy707-3790H     IWVNK (SEQ ID NO: 2)
Amy707-3156D     IWVNK (SEQ ID NO: 5)
Amy707-4037D     IWVNK (SEQ ID NO: 4)
                 *****
```

(continued)

α-AMYLASE VARIANTS

FIELD OF THE INVENTION

Disclosed are compositions and methods relating to variant α-amylases. The variant α-amylases are useful, for example, for starch liquefaction and saccharification, cleaning starchy stains, textile desizing, baking and brewing.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

α-amylases hydrolyze starch, glycogen, and related polysaccharides by cleaving internal α-1,4-glucosidic bonds at random. α-amylases, particularly from Bacilli, have been used for a variety of different purposes, including starch liquefaction and saccharification, textile desizing, starch modification in the paper and pulp industry, brewing, baking, production of syrups for the food industry, production of feedstocks for fermentation processes, and in animal feed to increase digestability. These enzymes can also be used to remove starchy soils and stains during dishwashing and laundry washing.

Numerous publications have described mutations in α-amylases. However, the need continues to exist for more robust engineered α-amylases molecules.

SUMMARY

The present compositions and methods relate to variant amylase polypeptides, and methods of use, thereof. Aspects and embodiments of the present compositions and methods are summarized in the following separately-numbered paragraphs:

1. In one aspect, a recombinant variant α-amylase is provided, comprising an amino acid sequence having at least 90% amino acid sequence identity to the amino acid sequence of SEQ ID NO: 2, SEQ ID NO: 3, SEQ ID NO: 4, SEQ ID NO: 5 or SEQ ID NO: 6, excluding the wild-type Amy707 enzyme, the wild-type *Bacillus* sp. AA560 enzyme, and known variants, thereof.

2. In some embodiments, the variant α-amylase of paragraph 1 comprises an amino acid sequence having at least 96% amino acid sequence identity to the amino acid sequence of SEQ ID NO: 2, SEQ ID NO: 3, SEQ ID NO: 4, SEQ ID NO: 5 or SEQ ID NO: 6.

3. In another aspect, a variant α-amylase encoded by a polynucleotide having at least 90% nucleic acid sequence identity to the polynucleotide of SEQ ID NO: 8, SEQ ID NO: 9, SEQ ID NO: 10, SEQ ID NO: 11 or SEQ ID NO: 12, or encoded by a polynucleotide that hybridizes under stringent conditions to the polynucleotide of SEQ ID NO: 8, SEQ ID NO: 9, SEQ ID NO: 10, SEQ ID NO: 11 or SEQ ID NO: 12, or the complement, thereof, is provided.

4. In another aspect, a polynucleotide having at least 90% nucleic acid sequence identity to the polynucleotide of SEQ ID NO: 8, SEQ ID NO: 9, SEQ ID NO: 10, SEQ ID NO: 11 or SEQ ID NO: 12, an expression vector comprising the polynucleotide, or an expression host comprising the polynucleotide or the expression vector is provided.

5. In another aspect, a composition for liquefying starch comprising the variant amylase of any of paragraphs 1-3 is provided.

6. In another aspect, a detergent composition comprising the variant amylase of any of paragraphs 1-3 is provided.

7. In another aspect, a method for converting starch to oligosaccharides, comprising contacting starch with effective amount of the variant amylase of any of paragraphs 1-3 is provided.

8. In another aspect, a method for removing a starchy stain or soil from a surface is provided, comprising contacting the surface with an effective amount of the variant amylase of any of paragraphs 1-3, and allowing the polypeptide to hydrolyze starch components present in the starchy stain to produce smaller starch-derived molecules that dissolve in the aqueous composition, thereby removing the starchy stain from the surface.

These and other aspects and embodiments of the compositions and methods will be apparent from the present description and drawings.

BRIEF DESCRIPTION OF THE DRAWINGS

FIG. 1 shows a Clustal W amino acid sequence alignment of Amy707, Amy707-3790H, Amy707-2170D, Amy707-4037D, Amy707-3156D and Amy707-3915D.

DETAILED DESCRIPTION

Described are compositions and methods relating to variant α-amylase enzymes. Exemplary applications for the variant amylase enzymes are for starch liquefaction and saccharification, for cleaning starchy stains in laundry, dishwashing, and other applications, for textile processing (e.g., desizing), in animal feed for improving digestibility, and for baking and brewing. These and other aspects of the compositions and methods are described in detail, below.

Prior to describing the various aspects and embodiments of the present compositions and methods, the following definitions and abbreviations are described.

1. Definitions and Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art. The following terms are defined, below, for clarity.

1.1. Abbreviations and Acronyms

The following abbreviations/acronyms have the following meanings unless otherwise specified:

DNA deoxyribonucleic acid
EC Enzyme Commission
FH French hardness
GA glucoamylase GH general hardness
HDL high density liquid detergent
HDD heavy duty powder detergent
HSG high suds granular detergent
HFCS high fructose corn syrup
IRS insoluble residual starch
kDa kiloDalton
MW molecular weight
MWU modified Wohlgemuth unit; $1.6 \times 10^{-5}$ mg/MWU=unit of activity
NCBI National Center for Biotechnology Information
PI performance index
ppm parts per million, e.g., μg protein per gram dry solid
RCF relative centrifugal/centripetal force (i.e., x gravity)
sp. species
Tm melting temperature
w/v weight/volume
w/w weight/weight
v/v volume/volume
wt % weight percent
° C. degrees Centigrade
$H_2O$ water
$dH_2O$ or DI deionized water
$dIH_2O$ deionized water, Milli-Q filtration
g or gm grams
μg micrograms
mg milligrams
kg kilograms
μL and μl microliters
mL and ml milliliters
mm millimeters
μm micrometer
M molar
mM millimolar
μM micromolar
U units
sec seconds
min(s) minute/minutes
hr(s) hour/hours
ETOH ethanol
N normal
MWCO molecular weight cut-off
CAZy Carbohydrate-Active Enzymes database

1.2. Definitions

The terms "amylase" or "amylolytic enzyme" refer to an enzyme that is, among other things, capable of catalyzing the degradation of starch. α-amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion yielding polysaccharides containing three or more (1-4)-α-linked D-glucose units. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

The term "starch" refers to any material comprised of the complex polysaccharide carbohydrates of plants, comprised of amylose and amylopectin with the formula $(C_6H_{10}O_5)_x$, wherein X can be any number. The term includes plant-based materials such as grains, cereal, grasses, tubers and roots, and more specifically materials obtained from wheat, barley, corn, rye, rice, sorghum, brans, cassava, millet, milo, potato, sweet potato, and tapioca. The term "starch" includes granular starch. The term "granular starch" refers to raw, i.e., uncooked starch, e.g., starch that has not been subject to gelatinization.

As used herein, the term "liquefaction" or "liquefy" means a process by which starch is converted to less viscous and shorter chain dextrins.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type polypeptide is understood to include the mature form of the polypeptide. A "mature" polypeptide or variant, thereof, is one in which a signal sequence is absent, for example, cleaved from an immature form of the polypeptide during or following expression of the polypeptide.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

In the case of the present α-amylases, "activity" refers to α-amylase activity, which can be measured as described, herein.

The term "performance benefit" refers to an improvement in a desirable property of a molecule. Exemplary performance benefits include, but are not limited to, increased hydrolysis of a starch substrate, increased grain, cereal or other starch substrate liquifaction performance, increased cleaning performance, increased thermal stability, increased detergent stability, increased storage stability, increased solubility, an altered pH profile, decreased calcium dependence, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

The terms "protease" and "proteinase" refer to an enzyme protein that has the ability to perform "proteolysis" or "proteolytic cleavage" which refers to hydrolysis of peptide bonds that link amino acids together in a peptide or polypeptide chain forming the protein. This activity of a protease as a protein-digesting enzyme is referred to as "proteolytic activity."

The terms "serine protease" refers to enzymes that cleave peptide bonds in proteins, in which enzymes serine serves as the nucleophilic amino acid at the enzyme active site. Serine proteases fall into two broad categories based on their structure: chymotrypsin-like (trypsin-like) or subtilisin-like. Most commonly used in laundry and dishwashing detergents are serine protease, particularly subtlisins.

"Combinatorial variants" are variants comprising two or more mutations, e.g., 2, 3, 4, 5, 6, 7, 8, 9, 10, or more, substitutions, deletions, and/or insertions.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an amylase is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptides, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 90% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t\frac{1}{2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may contain chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na3 citrate, pH 7.0). Hybridized, duplex nucleic acids are characterized by a melting temperature (Tm), where one half of the hybridized nucleic acids are unpaired with the complementary strand. Mismatched nucleotides within the duplex lower the Tm. A nucleic acid encoding a variant α-amylase may have a Tm reduced by 1° C.-3° C. or more compared to a duplex formed between the nucleotide of SEQ ID NO: 2 and its identical complement.

A "synthetic" molecule is produced by in vitro chemical or enzymatic synthesis rather than by an organism.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Biologically active" refer to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein.

As used herein, "water hardness" is a measure of the minerals (e.g., calcium and magnesium) present in water.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme.

"A cultured cell material comprising an amylase" or similar language, refers to a cell lysate or supernatant (including media) that includes an amylase as a component. The cell material may be from a heterologous host that is grown in culture for the purpose of producing the amylase.

"Percent sequence identity" means that a particular sequence has at least a certain percentage of amino acid residues identical to those in a specified reference sequence, when aligned using the CLUSTAL W algorithm with default parameters. See Thompson et al. (1994) Nucleic Acids Res. 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Deletions are counted as non-identical residues, compared to a reference sequence.

"Fused" polypeptide sequences are connected, i.e., operably linked, via a peptide bond between two subject polypeptide sequences.

The term "filamentous fungi" refers to all filamentous forms of the subdivision Eumycotina, particulary Pezizomycotina species.

The term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

An "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or fungal fermentation. "Beer" is an example of such a fermented beverage, and the term "beer" is meant to comprise any fermented worth produced by fermentation/brewing of a starch-containing plant material. Often, beer is produced exclusively from malt or adjunct, or any combination of malt and adjunct.

The term "malt" refers to any malted cereal grain, such as malted barley or wheat.

The term "adjunct" refers to any starch and/or sugar containing plant material that is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

The term "about" refers to ±15% to the referenced value.

2. α-Amylase Variants

An aspect of the present compositions and methods is variant α-amylase enzymes that include combinations of mutations that improve their performance in industrial applications. The variants are most closely related to an α-amylase from a *Bacillus* sp. 707, herein, referred to as "Amy707." The amino acid sequence of Amy707 α— is shown, below, as SEQ ID NO: 1:

```
HHNGTNGTMMQYFEWYLPNDGNHWNRLNSDASNLKSKGITAVWIPPAWKG
ASQNDVGYGAYDLYDLGEFNQKGTVRTKYGTRSQLQAAVTSLKNNGIQVY
GDVVMNHKGGADATEMVRAVEVNPNNRNQEVTGEYTIEAWTRFDFPGRGN
THSSFKWRWYHFDGVDWDQSRRLNNRIYKFRGHGKAWDWEVDTENGNYDY
LMYADIDMDHPEVVNELRNWGVWYTNTLGLDGFRIDAVKHIKYSFTRDWI
NHVRSATGKNMFAVAEFWKNDLGAIENYLQKTNWNHSVFDVPLHYNLYNA
SKSGGNYDMRNIFNGTVVQRHPSHAVTFVDNHDSQPEEALESFVEEWFKP
LAYALTLTREQGYPSVFYGDYYGIPTHGVPAMRSKIDPILEARQKYAYGK
QNDYLDHHNIIGWTREGNTAHPNSGLATIMSDGAGGSKWMFVGRNKAGQV
WSDITGNRTGTVTINADGWGNFSVNGGSVSIWVNK
```

In some embodiments, the variant α-amylase is Amy707-3790H, having the amino acid sequence shown below, as SEQ ID NO: 2:

```
HHNGTNGTMMQYFEWYLPNDGNHWNRLNSDASNLKSKGITAVWIPPAYKG
TSQNDVGYGAYDLYDLGEFNQKGTVRTKYGTRSQLQAAVTSLKNNGIQVY
GDVVMNHKGGADATEMVRAVEVNPSNRNQEISGDYTIEAWTKFDFPGRGN
THSSFKWRWYHFDGVDWDQSRRLNNRIYKFHGKAWDWPVSSENGNYDYLM
YADIDMDHPDVVNELRNWGVWYANTLGLDGFRIDAVKHIKYSFTRDWINH
VRSATGKNMFAVAEFWKNDLGAIENYLQKTNWNHSVFDVPLHYNLYNASK
SGGNYDMRNIFNGTVVQRHPSHAVTFVDNHDSQPEEALESFVEEWFKPLA
YALTLTREQGYPSVFYGDYYGIPTHGVPAMRSKIDPILEARQKYAYGKQN
DYLDHHNIIGWTREGNTAHPNSGLATIMSDGAGGSKWMNVGKNNAGEVWY
DITGNRTGTVTINADGWGQFHVNGGSVSIWVNK
```

In some embodiments, the variant α-amylase has at least 90%, at least 91%, at least 92%, at least 93%, at least 94%, at least 95%, at least 96%, at least 97%, at least 98%, or even at least 99% amino acid sequence identity to SEQ ID NO: 2, excluding the wild-type Amy707 enzyme, the wild-type *Bacillus* sp. AA560 enzyme, and known variants, thereof. In particular embodiments, the variant α-amylase has at least 96%, at least 97%, at least 98%, or even at least 99% amino acid sequence identity to SEQ ID NO: 2.

In some embodiments, the variant α-amylase is Amy707-2170D, having the amino acid sequence shown below, as SEQ ID NO: 3:

```
HHNGTNGTMMQYFEWYLPNDGNHWNRLNSDASNLKSKGITAVWIPPAWKG
ASQNDVGYGAYDLYDLGEFNQKGTVRTKYGTRSQLQAAVTSLKNNGIQVY
GDVVMNHKGGADYTETVTAVEVNPNNRNQETSGEYNIQAWTRFDFPGRGN
THSSFKWRWYHFDGVDWDQSRRLNNRIYKFDGKAWDWPVSSENGNYDYLM
YADVDFEHPEVVNEMKKWGVWYTNTLGLDGFRIDAVKHIKYSFTRDWINH
VRSATGKNMFAVAEFWKNDLGAIENYLQKTNWNHSVFDVPLHYNLYNASK
SGGNYDMRNIFNGTVVQRHPSHAVTFVDNHDSQPEEALESFVEEWFKPLA
YALTLTREQGYPSVFYGDYYGIPTHGVPAMRSKIDPILEARQKYAYGKQN
DYLDHHNIIGWTREGNTAHPNSGLATLISDGPGGSKWMFVGRNKAGQVWS
DITGNRTGTVTINADGWGNFSVNGGSVSIWVNK
```

In some embodiments, the variant α-amylase has at least 90%, at least 91%, at least 92%, at least 93%, at least 94%, at least 95%, at least 96%, at least 97%, at least 98%, or even at least 99% amino acid sequence identity to SEQ ID NO: 3, excluding the wild-type Amy707 enzyme, the wild-type *Bacillus* sp. AA560 enzyme, and known variants, thereof. In particular embodiments, the variant α-amylase has at least 96%, at least 97%, at least 98%, or even at least 99% amino acid sequence identity to SEQ ID NO: 3.

In some embodiments, the variant α-amylase is Amy707-4037D, having the amino acid sequence shown below, as SEQ ID NO: 4:

```
HHNGTNGTMMQYFEWYLPNDGNHWNRLNSDASNLKSKGITAVWIPPAWKG
TSQNDVGYGAYDLYDLGEFNQKGTVRTKYGTRSQLQAAVTSLKNNGIQVY
GDVVMNHKGGADATEMVRAVEVNPNNRNQEVTGEYTIEAWTRFDFPGRGN
THSNFKWRWYHFDGVDWDQSRRLNNRIYKFDGKAWDWPVSSENGNYDYLM
YADLDFDHPDVANEMKNWGTWYANELNLDGFRLDAVKHIDHEYLRDWVNH
VRQQTGKNMFAVAEFWKNDLGAIENYLQKTNWNQSVFDAPLHYNLYNASK
SGGNYDMRNIFNGTVVQRHPSHAVTFVDNHDSQPEEALESFVEEWFKPLA
YALTLTREQGYPSVFYGDYYGIPTHGVPAMRSKIDPILEARQKYAYGKQN
DYLDHHNIIGWTREGDSTKANSGLATIMSDGPGGSKWMNVGKQNAGEVWY
DITGNRTGTVTINSDGWGQFFVNGGSVSIWVNK
```

In some embodiments, the variant α-amylase has at least 90%, at least 91%, at least 92%, at least 93%, at least 94%, at least 95%, at least 96%, at least 97%, at least 98%, or even at least 99% amino acid sequence identity to SEQ ID NO: 4, excluding the wild-type Amy707 enzyme, the wild-type *Bacillus* sp. AA560 enzyme, and known variants, thereof. In particular embodiments, the variant α-amylase has at least 96%, at least 97%, at least 98%, or even at least 99% amino acid sequence identity to SEQ ID NO: 4.

In some embodiments, the variant α-amylase is Amy707-3156D, having the amino acid sequence shown below, as SEQ ID NO: 5:

```
HHNGTNGTLMQYFEWYAPNDGQHWNRLRSDAENLAQKGITAVWIPPAWKG
ASQNDVGYGAYDLYDLGEFNQKGTVRTKYGTKAQLKSAVTSLKNNGIQVY
GDVVMNHKGGADATETVTAVEVNPSNRNQETSGEYNIQAWTRFDFPGRGN
THSSFKWRWYHFDGTDWDQSRRLNNRIYKFDGKAWDWPVSSENGNYDYLM
YADIDMDHPEVVNELRNWGVWYTNTLGLDGFRIDAVKHIKYSFTRDWINH
VRSATGKNMFAVAEFWKNDLGAIENYLQKTNWNHSVFDVPLHYNLYNASK
```

-continued

SGGNYDMRNIFNGTVVQRHPSHAVTFVDNHDSQPEEALESFVEEWFKPLA

YALTLTREQGYPSVFYGDYYGIPTHGVPAMRSKIDPILEARQKYAYGKQN

DYLDHHNIIGWTREGDSTKANSGLATIMSDGPGGSKWMNVGKNNAGQVWS

DITGNRTGTVTINADGWGQFFVNGGSVSIWVNK

In some embodiments, the variant α-amylase has at least 90%, at least 91%, at least 92%, at least 93%, at least 94%, at least 95%, at least 96%, at least 97%, at least 98%, or even at least 99% amino acid sequence identity to SEQ ID NO: 5, excluding the wild-type Amy707 enzyme, the wild-type *Bacillus* sp. AA560 enzyme, and known variants, thereof. In particular embodiments, the variant α-amylase has at least 96%, at least 97%, at least 98%, or even at least 99% amino acid sequence identity to SEQ ID NO: 5.

In some embodiments, the variant α-amylase is Amy707-3915D, having the amino acid sequence shown below, as SEQ ID NO: 6:

ATVNNGTLMQYFEWYLPNDGQHWNRLNSDASNLKSKGITAVWIPPAYKGT

TQNDVGYGAYDLYDLGEFNQKGTVRTKYGTRSQLQAAVTSLKNNGIQVYG

DAVMNHKGGADATEMVRAVEVNPSNRNQETSGEYNIQAWTGFNFPGRGNT

HSSFKWRWYHFDGVDWDQSRRLNNRIYKFDGKAWDWPVSSENGNYDYLMY

ADLDFDHPDVVNEMKEWGVWYANTLGLDGFRIDAVKHIKYSFTRDWINHV

RSATGKNMFAVAEFWKNDLGAIENYLQKTNWNHSVFDVPLHYNLYNASKS

GGNYDMRNIFNGTVVQRHPSHAVTFVDNHDSQPEEALESFVEEWFKPLAY

ALTLTREQGYPSVFYGDYYGIPTHGVPAMRSKIDPILEARQKYAYGKQND

YLDHHNIIGWTREGNTAHPNSGLATIMSDGPGGSKWMFVGRNKAGQVWSD

ITGNRTGTVTINADGWGNFSVNGGSVSIWVNK

In some embodiments, the variant α-amylase has at least 90%, at least 91%, at least 92%, at least 93%, at least 94%, at least 95%, at least 96%, at least 97%, at least 98%, or even at least 99% amino acid sequence identity to SEQ ID NO: 6, excluding the wild-type Amy707 enzyme, the wild-type *Bacillus* sp. AA560 enzyme, and known variants, thereof. In particular embodiments, the variant α-amylase has at least 96%, at least 97%, at least 98%, or even at least 99% amino acid sequence identity to SEQ ID NO: 6.

The amino acid sequence of the α-amylase from *Bacillus* sp. AA560 is shown below, as SEQ ID NO: 7:

HHNGTNGTMMQYFEWYLPNDGNHWNRLRSDASNLKDKGISAVWIPPAWKG

ASQNDVGYGAYDLYDLGEFNQKGTIRTKYGTRNQLQAAVNALKSNGIQVY

GDVVMNHKGGADATEMVRAVEVNPNNRNQEVSGEYTIEAWTKFDFPGRGN

THSNFKWRWYHFDGVDWDQSRKLNNRIYKFRGDGKGWDWEVDTENGNYDY

LMYADIDMDHPEVVNELRNWGVWYTNTLGLDGFRIDAVKHIKYSFTRDWI

NHVRSATGKNMFAVAEFWKNDLGAIENYLNKTNWNHSVFDVPLHYNLYNA

SKSGGNYDMRQIFNGTVVQRHPMHAVTFVDNHDSQPEEALESFVEEWFKP

LAYALTLTREQGYPSVFYGDYYGIPTHGVPAMKSKIDPILEARQKYAYGR

QNDYLDHHNIIGWTREGNTAHPNSGLATIMSDGAGGNKWMFVGRNKAGQV

WTDITGNRAGTVTINADGWGNFSVNGGSVSIWVNK

An amino acid sequence alignment of Amy707, Amy707-3790H, Amy707-2170D, Amy707-4037D, Amy707-3156D and Amy707-3915D, is shown in FIG. 1.

The present amylases may include any number of conservative amino acid substitutions. Exemplary conservative amino acid substitutions are listed in Table 1.

TABLE 1

Conservative amino acid substitutions

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S—Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S—Me-Cys, He, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

It will be appreciated that some of the above mentioned conservative mutations can be produced by genetic manipulation, while others are produced by introducing synthetic amino acids into a polypeptide by genetic or other means.

The present amylase may also be derived from any of the above-described amylase variants by substitution, deletion or addition of one or several amino acids in the amino acid sequence, for example less than 10, less than 9, less than 8, less than 7, less than 6, less than 5, less than 4, less than 3, or even less than 2 substitutions, deletions or additions. Such variants should have the same activity as amylase from which they were derived.

The present amylase may be "precursor," "immature," or "full-length," in which case they include a signal sequence, or "mature," in which case they lack a signal sequence. Mature forms of the polypeptides are generally the most useful. Unless otherwise noted, the amino acid residue numbering used herein refers to the mature forms of the respective amylase polypeptides. The present amylase polypeptides may also be truncated to remove the N or C-termini, so long as the resulting polypeptides retain amylase activity.

The present amylase may be a "chimeric," "hybrid" or "domain swap" polypeptide, in that it includes at least a portion of a first amylase polypeptide, and at least a portion of a second amylase polypeptide. The present amylases may further include heterologous signal sequence, an epitope to allow tracking or purification, or the like. Exemplary heterologous signal sequences are from *B. licheniformis* amylase (LAT), *B. subtilis* (AmyE or AprE), and *Streptomyces* CelA.

2.5. Nucleotides Encoding Variant Amylase Polypeptides

In another aspect, nucleic acids encoding a variant amylase polypeptide are provided. The nucleic acid may encode a particular amylase polypeptide, or an amylase having a specified degree of amino acid sequence identity to the particular amylase.

In some embodiments, the nucleic acid encodes an amylase having at least 90%, at least 91%, at least 92%, at least 93%, at least 94%, at least 95%, at least 96%, at least 97%, at least 98%, or even at least 99% amino acid sequence identity to SEQ ID NO: 2, 3, 4, 5 or 6. It will be appreciated that due to the degeneracy of the genetic code, a plurality of nucleic acids may encode the same polypeptide.

In some embodiments, the nucleic acid itself has at least 90%, at least 91%, at least 92%, at least 93%, at least 94%, at least 95%, at least 96%, at least 97%, at least 98%, or even at least 99% nucleic acid sequence identity to SEQ ID NO: 8, 9, 10, 11 or 12, which are shown, below.

In some embodiments, the nucleic acid hybridizes under stringent or very stringent conditions to a nucleic acid encoding (or complementary to a nucleic acid encoding) an amylase having at least 91%, at least 92%, at least 93%, at least 94%, at least 95%, at least 96%, at least 97%, at least 98% or even at least 99% nucleic acid sequence identity to SEQ ID NO: 8, 9, 10, 11 or 12.

The DNA sequence encoding the mature form of Amy707-3790H is shown, below, as SEQ ID NO: 8:

```
CATCATAACGGTACAAACGGAACAATGATGCAGTATTTCGAGTGGTATCT
ACCTAACGACGGCAATCATTGGAACAGACTGAACTCAGATGCCAGTAACT
TGAAATCTAAAGGTATTACAGCAGTATGGATTCCGCCGGCTTATAAGGGC
ACGTCTCAAAATGATGTGGGGTACGGCGCATACGATCTGTATGATTTAGG
CGAGTTTAATCAAAAAGGTACAGTCAGAACGAAGTATGGCACAAGAAGTC
AACTTCAAGCCGCTGTTACCTCGCTGAAAAATAATGGAATCCAAGTGTAT
GGTGATGTCGTGATGAATCATAAAGGAGGTGCTGATGCTACAGAAATGGT
AAGGGCGGTGGAGGTGAATCCGTCTAATAGAAATCAGGAAATTAGCGGCG
ATTATACAATTGAAGCATGGACAAAATTCGATTTTCCGGGCCGAGGAAAT
ACGCATTCTAGCTTCAAATGGAGGTGGTACCATTTTGATGGAGTGGATTG
GGACCAGAGCAGAAGACTCAACAATAGAATCTACAAATTCCATGGAAAGG
CGTGGGACTGGCCGGTTTCTTCAGAAAACGGAAATTATGACTATCTGATG
TACGCGGACATTGATATGGACCATCCGGATGTCGTGAATGAATTGAGAAA
TTGGGGCGTCTGGTATGCCAACACATTAGGGTTAGATGGATTCAGAATTG
ACGCGGTCAAACATATTAAATATAGCTTTACCAGAGACTGGATTAATCAC
GTAAGATCAGCGACGGGAAAAAATATGTTTGCGGTTGCCGAATTTTGAA
AAATGATTTAGGGGCCATTGAAAACTACCTGCAAAAGACAAATTGGAACC
ATTCTGTTTTTGATGTGCCGTTGCATTACAACCTTTACAATGCCTCAAAA
AGCGGTGGAAATTACGATATGAGAAATATTTTTAATGGCACGGTAGTCCA
ACGCCATCCGAGTCATGCTGTTACGTTTGTTGATAATCATGACTCACAGC
CTGAAGAAGCACTGGAATCATTTGTCGAAGAGTGGTTTAAACCGTTAGCC
TATGCGCTTACTCTCACGAGAGAACAAGGCTATCCTTCTGTATTTTATGG
AGATTATTACGGTATTCCAACACATGGGGTCCCTGCTATGAGATCTAAAA
TCGATCCTATTCTTGAGGCTAGACAAAAGTATGCTTATGGAAAACAGAAT
GACTATTTAGATCACCATAATATCATTGGCTGGACGAGAGAAGGGAACAC
AGCGCACCCCAATAGCGGTCTGGCCACAATCATGTCAGATGGGGCGGGCG
GTTCAAAATGGATGAATGTTGGCAAAAATAATGCGGGTGAAGTTTGGTAT
GATATTACAGGGAATAGAACAGGTACAGTCACGATTAATGCCGATGGCTG
GGGCCAATTTCATGTCAATGGGGGCTCAGTTTCAATATGGGTGAACAAAT
GA
```

The DNA sequence encoding the mature form of Amy707-2170D is shown, below, as SEQ ID NO: 9:

```
CATCATAACGGTACGAACGGGACAATGATGCAATACTTTGAATGGTATCT
ACCTAATGACGGAAATCATTGGAATCGATTAAACTCTGATGCGAGTAACC
TTAAAAGCAAAGGGATTACAGCGGTGTGGATTCCTCCAGCATGGAAGGGC
GCTTCTCAAAATGACGTAGGATACGGAGCCTATGACCTGTATGATCTGGG
AGAATTTAATCAAAAAGGTACCGTCCGTACAAAATATGGAACACGTAGTC
AGTTACAAGCTGCGGTAACCTCCTTAAAAAATAATGGAATTCAAGTATAT
GGTGACGTTGTTATGAATCACAAAGGTGGCGCAGACTATACTGAAACAGT
AACGGCCGTTGAAGTGAATCCCAATAACCGTAACCAAGAAACATCTGGTG
AATATAATATTCAAGCTTGGACTAGATTTGATTTTCCAGGGCGAGGAAAT
ACTCATTCTAGCTTTAAATGGAGATGGTATCATTTTGATGGTGTGGATTG
GGATCAGTCACGTAGACTGAACAATCGCATCTATAAATTTGATGGCAAAG
CTTGGGATTGGCCAGTTAGTTCTGAAAATGGTAATTATGATTATTTGATG
TACGCTGATGTTGATTTTGAACACCCAGAAGTAGTAAATGAAATGAAAAA
GTGGGGTGTTTGGTACACAAACACATTAGGACTCGATGGATTTAGAATAG
ATGCGGTTAAACATATAAAGTATAGCTTTACGCGCGATTGGATTAATCAC
GTTAGAAGTGCAACAGGTAAAAATATGTTTGCGGTTGCTGAGTTTTGGAA
GAATGATTTAGGTGCAATTGAAAACTATCTGCAGAAAACAAACTGGAACC
ATTCAGTCTTTGATGTGCCGTTACATTATAATCTGTATAATGCATCAAAA
AGCGGAGGGAACTATGATATGCGAAACATATTTAATGGAACGGTTGTTCA
ACGACATCCAAGTCATGCTGTAACATTTGTTGATAATCATGATTCGCAGC
CTGAAGAAGCATTAGAATCTTTTGTTGAAGAATGGTTTAAACCATTAGCG
TATGCGCTTACATTAACGCGTGAACAAGGATACCCTTCTGTATTTTACGG
AGATTATTATGGGATTCCAACACATGGAGTGCCAGCAATGAGATCAAAAA
TCGATCCGATTTTAGAAGCACGTCAAAAGTATGCATACGGAAAACAAAAT
GATTACTTAGACCATCATAATATCATTGGTTGGACGCGTGAAGGGAATAC
AGCACACCCCAATTCAGGTCTAGCTACCTTAATTTCTGATGGACCAGGTG
GAAGTAAGTGGATGTTTGTTGGGCGTAATAAGGCTGGTCAAGTATGGAGT
GATATTACAGGAACCGTACAGGTACGGTTACAATCAATGCAGACGGTTG
GGGCAATTTCTCTGTGAATGGAGGGTCAGTTTCTATTTGGGTCAACAAAT
AA
```

The DNA sequence encoding the mature form of Amy707-4037D is shown, below, as SEQ ID NO: 10:

CATCATAACGGTACGAACGGGACAATGATGCAATACTTTGAATGGTATCT
ACCTAATGACGGAAATCATTGGAATCGATTAAACTCTGATGCGAGTAACC
TTAAAAGCAAAGGGATTACAGCGGTGTGGATTCCTCCAGCATGGAAGGGC
ACATCTCAAAATGACGTAGGATACGGAGCCTATGACCTGTATGATCTGGG
AGAATTTAATCAAAAAGGTACCGTCCGTACAAAATATGGAACACGTAGTC
AGTTACAAGCTGCGGTAACCTCCTTAAAAAATAATGGAATTCAAGTATAT
GGTGACGTTGTTATGAATCACAAAGGTGGCGCAGACGCTACTGAAATGGT
AAGGGCCGTTGAAGTGAATCCCAATAACCGTAACCAAGAAGTGACTGGTG
AATATACCATTGAAGCTTGGACTAGATTTGATTTTCCAGGGCGAGGAAAT
ACTCATTCTAATTTTAAATGGAGATGGTATCATTTTGATGGTGTGGATTG
GGATCAGTCACGTAGACTGAACAATCGCATCTATAAATTTGATGGCAAAG
CTTGGGATTGGCCAGTTTCATCTGAAAATGGTAATTATGATTATTTGATG
TACGCTGATTTAGATTTTGATCACCCAGATGTAGCAAATGAAATGAAAAA
TTGGGGTACATGGTACGCAAACGAATTAAATCTCGATGGATTTAGATTAG
ATGCGGTTAAACATATAGATCATGAATATTTACGCGATTGGGTTAATCAC
GTTAGACAACGACAGGTAAAAATATGTTTGCGGTTGCTGAGTTTTGGAA
GAATGATTTAGGTGCAATTGAAAACTATCTGCAGAAAACAAACTGGAACC
AATCAGTCTTTGATGCTCCGTTACATTATAATCTGTATAATGCATCAAAA
AGCGGAGGGAACTATGATATGCGAAACATATTTAATGGAACGGTTGTTCA
ACGACATCCAAGTCATGCTGTAACATTTGTTGATAATCATGATTCGCAGC
CTGAAGAAGCATTAGAATCTTTTGTTGAAGAATGGTTTAAACCATTAGCG
TATGCGCTTACATTAACGCGTGAACAAGGATACCCTTCTGTATTTTACGG
AGATTATTATGGGATTCCAACACATGGAGTGCCAGCAATGAGATCAAAAA
TCGATCCGATTTTAGAAGCACGTCAAAAGTATGCATACGGAAAACAAAT
GATTACTTAGACCATCATAATATCATTGGTTGGACGCGTGAAGGGGATAG
TACAAAAGCAAATTCAGGTCTAGCTACCATCATGTCTGATGGACCAGGTG
GAAGTAAGTGGATGAATGTTGGGAAACAAAATGCTGGTGAAGTATGGTAT
GATATTACAGGAAACCGTACAGGTACGGTTACAATCAATTCTGACGGTTG
GGGCCAATTCTTTGTGAATGGAGGGTCAGTTTCTATTTGGGTCAACAAAT
AA

The DNA sequence encoding the mature form of Amy707-3156D is shown, below, as SEQ ID NO: 11:

CATCATAACGGTACGAACGGGACATTAATGCAATACTTTGAATGGTATGC
ACCTAATGACGGACAACATTGGAATCGATTAAGATCTGATGCGGAAAACC
TTGCGCAAAAGGGATTACAGCGGTGTGGATTCCTCCAGCATGGAAGGGC
GCTTCTCAAAATGACGTAGGATACGGAGCCTATGACCTGTATGATCTGGG
AGAATTTAATCAAAAAGGTACCGTCCGTACAAAATATGGAACAAAAGCGC
AGTTAAAAAGTGCGGTAACCTCCTTAAAAAATAATGGAATTCAAGTATAT
GGTGACGTTGTTATGAATCACAAAGGTGGCGCAGACGCTACTGAAACAGT
AACGGCCGTTGAAGTGAATCCCTCTAACCGTAACCAAGAAACATCAGGTG
AATATAATATTCAAGCTTGGACTAGATTTGATTTTCCAGGGCGAGGAAAT
ACTCATTCTAGCTTTAAATGGAGATGGTATCATTTTGATGGTACAGATTG
GGATCAGTCACGTAGACTGAACAATCGCATCTATAAATTTGATGGCAAAG
CTTGGGATTGGCCAGTTAGTTCTGAAAATGGTAATTATGATTATTTGATG
TACGCTGATATTGATATGGATCACCCAGAAGTAGTAAATGAATTAAGAAA
TTGGGGTGTTTGGTACACAAACACATTAGGACTCGATGGATTTAGAATAG
ATGCGGTTAAACATATAAAGTATAGCTTTACGCGCGATTGGATTAATCAC
GTTAGAAGTGCAACAGGTAAAAATATGTTTGCGGTTGCTGAGTTTTGGAA
GAATGATTTAGGTGCAATTGAAAACTATCTGCAGAAAACAAACTGGAACC
ATTCAGTCTTTGATGTGCCGTTACATTATAATCTGTATAATGCATCAAAA
AGCGGAGGGAACTATGATATGCGAAACATATTTAATGGAACGGTTGTTCA
ACGACATCCAAGTCATGCTGTAACATTTGTTGATAATCATGATTCGCAGC
CTGAAGAAGCATTAGAATCTTTTGTTGAAGAATGGTTTAAACCATTAGCG
TATGCGCTTACATTAACGCGTGAACAAGGATACCCTTCTGTATTTTACGG
AGATTATTATGGGATTCCAACACATGGAGTGCCAGCAATGAGATCAAAAA
TCGATCCGATTTTAGAAGCACGTCAAAAGTATGCATACGGAAAACAAAT
GATTACTTAGACCATCATAATATCATTGGTTGGACGCGTGAAGGGGATTC
TACAAAAGCAAATTCAGGTCTAGCTACCATCATGTCTGATGGACCAGGTG
GAAGTAAGTGGATGAATGTTGGGAAAAATAATGCTGGTCAAGTATGGAGT
GATATTACAGGAAACCGTACAGGTACGGTTACAATCAATGCAGACGGTTG
GGGCCAATTCTTTGTGAATGGAGGGTCAGTTTCTATTTGGGTCAACAAAT
AA

The DNA sequence encoding the mature form of Amy707-3915D is shown, below, as SEQ ID NO: 12:

GCAACAGTGAATAACGGGACATTAATGCAATACTTTGAATGGTATCTACC
TAATGACGGACAACATTGGAATCGATTAAACTCTGATGCGAGTAACCTTA
AAAGCAAAGGGATTACAGCGGTGTGGATTCCTCCAGCATATAAGGGCACA
ACGCAAAATGACGTAGGATACGGAGCCTATGACCTGTATGATCTGGGAGA
ATTTAATCAAAAAGGTACCGTCCGTACAAAATATGGAACACGTAGTCAGT
TACAAGCTGCGGTAACCTCCTTAAAAAATAATGGAATTCAAGTATATGGT
GACGCGGTTATGAATCACAAAGGTGGCGCAGACGCTACTGAAATGGTAAG
GGCCGTTGAAGTGAATCCCTCTAACCGTAACCAAGAAACATCTGGTGAAT
ATAATATTCAAGCTTGGACTGATTTAATTTTCCAGGGCGAGGAAATACT
CATTCTAGCTTTAAATGGAGATGGTATCATTTTGATGGTGTGGATTGGGA
TCAGTCACGTAGACTGAACAATCGCATCTATAAATTTGATGGCAAAGCTT
GGGATTGGCCAGTTAGTTCTGAAAATGGTAATTATGATTATTTGATGTAC
GCTGATTTAGATTTTGATCACCCAGATGTAGTAAATGAAATGAAGGAATG
GGGTGTTTGGTACGCAAACACATTAGGACTCGATGGATTTAGAATAGATG

```
-continued
CGGTTAAACATATAAAGTATAGCTTTACGCGCGATTGGATTAATCACGTT

AGAAGTGCAACAGGTAAAAATATGTTTGCGGTTGCTGAGTTTTGGAAGAA

TGATTTAGGTGCAATTGAAAACTATCTGCAGAAAACAAACTGGAACCATT

CAGTCTTTGATGTGCCGTTACATTATAATCTGTATAATGCATCAAAAAGC

GGAGGGAACTATGATATGCGAAACATATTTAATGGAACGGTTGTTCAACG

ACATCCAAGTCATGCTGTAACATTTGTTGATAATCATGATTCGCAGCCTG

AAGAAGCATTAGAATCTTTTGTTGAAGAATGGTTTAAACCATTAGCGTAT

GCGCTTACATTAACGCGTGAACAAGGATACCCTTCTGTATTTTACGGAGA

TTATTATGGGATTCCAACACATGGAGTGCCAGCAATGAGATCAAAATCG

ATCCGATTTTAGAAGCACGTCAAAAGTATGCATACGGAAAACAAAATGAT

TACTTAGACCATCATAATATCATTGGTTGGACGCGTGAAGGGAATACAGC

ACACCCCAATTCAGGTCTAGCTACCATCATGTCTGATGGACCAGGTGGAA

GTAAGTGGATGTTTGTTGGGCGTAATAAGGCTGGTCAAGTATGGAGTGAT

ATTACAGGAAACCGTACAGGTACGGTTACAATCAATGCAGACGGTTGGGG

CAATTTCTCTGTGAATGGAGGGTCAGTTTCTATTTGGGTCAACAAATAA
```

3. Production of Variant Amylases

The present variant amylases can be produced in host cells, for example, by secretion or intracellular expression, using methods well-known in the art. Fermentation, separation, and concentration techniques are well known in the art and conventional methods can be used to prepare a concentrated, variant-α-amylase-polypeptide-containing solution.

For production scale recovery, variant α-amylase polypeptides can be enriched or partially purified as generally described above by removing cells via flocculation with polymers. Alternatively, the enzyme can be enriched or purified by microfiltration followed by concentration by ultrafiltration using available membranes and equipment. However, for some applications, the enzyme does not need to be enriched or purified, and whole broth culture can be lysed and used without further treatment. The enzyme can then be processed, for example, into granules.

4. Compositions and Uses of Variant Amylases

Variants amylases are useful for a variety of industrial applications. For example, variant amylases are useful in a starch conversion process, particularly in a saccharification process of a starch that has undergone liquefaction. The desired end-product may be any product that may be produced by the enzymatic conversion of the starch substrate. For example, the desired product may be a syrup rich in glucose and maltose, which can be used in other processes, such as the preparation of HFCS, or which can be converted into a number of other useful products, such as ascorbic acid intermediates (e.g., gluconate; 2-keto-L-gluconic acid; 5-keto-gluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones.

The starch conversion process may be a precursor to, or simultaneous with, a fermentation process designed to produce alcohol for fuel or drinking (i.e., potable alcohol). One skilled in the art is aware of various fermentation conditions that may be used in the production of these end-products. Variant amylases are also useful in compositions and methods of food preparation. These various uses of variant amylases are described in more detail below.

4.1. Preparation of Starch Substrates

Methods for preparing starch substrates for use in the processes disclosed herein are well known. Useful starch substrates may be obtained from, e.g., tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may also be highly refined raw starch or feedstock from starch refinery processes.

4.2. Gelatinization and Liquefaction of Starch

Gelatinization is generally performed simultaneously with, or followed by, contacting a starch substrate with an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-amylase may be added to the slurry, with a metering pump, for example. To optimize α-amylase stability and activity, the pH of the slurry typically is adjusted to about pH 4.5-6.5 and about 1 mM of calcium (about 40 ppm free calcium ions) can also be added, depending upon the properties of the amylase used. α-amylase remaining in the slurry following liquefaction may be deactivated via a number of methods, including lowering the pH in a subsequent reaction step or by removing calcium from the slurry in cases where the enzyme is dependent upon calcium.

The slurry of starch plus the α-amylase may be pumped continuously through a jet cooker, which is steam heated to 105° C. The slurry is then allowed to cool to room temperature. This cooling step can be 30 minutes to 180 minutes, e.g., 90 minutes to 120 minutes. The liquefied starch typically is in the form of a slurry having a dry solids content (w/w) of about 10-50%; about 10-45%; about 15-40%; about 20-40%; about 25-40%; or about 25-35%.

Liquefaction with variant amylases advantageously can be conducted at low pH, eliminating the requirement to adjust the pH to about pH 5.5-6.5. Variants amylases can be used for liquefaction at a pH range of 2 to 7, e.g., pH 3.0-7.5, pH 4.0-6.0, or pH 4.5-5.8. Variant amylases can maintain liquefying activity at a temperature range of about 85° C.-95° C., e.g., 85° C., 90° C., or 95° C. For example, liquefaction can be conducted with 800 μg an amylase in a solution of 25% DS corn starch for 10 min at pH 5.8 and 85° C., or pH 4.5 and 95° C., for example. Liquefying activity can be assayed using any of a number of known viscosity assays in the art.

In particular embodiments using the present amylase variants, starch liquifaction is performed at a temperature range of 90-115° C., for the purpose of producing high-purity glucose syrups, HFCS, maltodextrins, etc.

4.3. Saccharification

The liquefied starch can be saccharified into a syrup that is rich in lower DP (e.g., DP1+DP2) saccharides, using variant amylases, optionally in the presence of another enzyme(s). The exact composition of the products of saccharification depends on the combination of enzymes used, as well as the type of granular starch processed. Advantageously, the syrup obtainable using the provided variant amylases may contain a weight percent of DP2 of the total oligosaccharides in the saccharified starch exceeding 30%, e.g., 45%-65% or 55%-65%. The weight percent of (DP1+DP2) in the saccharified starch may exceed about 70%, e.g., 75%-85% or 80%-85%. The present amylases also produce a relatively high yield of glucose, e.g., DP1>20%, in the syrup product.

Whereas liquefaction is generally run as a continuous process, saccharification is often conducted as a batch process. Saccharification typically is most effective at temperatures of about 60-65° C. and a pH of about 4.0-4.5, e.g., pH 4.3, necessitating cooling and adjusting the pH of the liquefied starch. The temperature and pH range can vary depending upon the properties of the enzymes. Saccharification may be performed, for example, at a temperature between about 40° C., about 50° C., or about 55° C. to about 60° C. or about 65° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a syrup typically is run over about 24-72 hours, for example, 24-48 hours. When a maximum or desired DE has been attained, the reaction is stopped by heating to 85° C. for 5 min., for example. Further incubation will result in a lower DE, eventually to about 90 DE, as accumulated glucose re-polymerizes to isomaltose and/or other reversion products via an enzymatic reversion reaction and/or with the approach of thermodynamic equilibrium. When using an amylase, saccharification optimally is conducted at a temperature range of about 30° C. to about 75° C., e.g., 45° C.-75° C. or 47° C.-74° C. The saccharifying may be conducted over a pH range of about pH 3 to about pH 7, e.g., pH 3.0-pH 7.5, pH 3.5-pH 5.5, pH 3.5, pH 3.8, or pH 4.5.

An α-amylase may be added to the slurry in the form of a composition. An α-amylase can be added to a slurry of a granular starch substrate in an amount of about 0.6-10 ppm ds, e.g., 2 ppm ds. An α-amylase can be added as a whole broth, clarified, enriched, partially purified, or purified enzyme. The specific activity of the amylase may be about 300 U/mg of enzyme, for example, measured with the PAHBAH assay. The α-amylase also can be added as a whole broth product.

An α-amylase may be added to the slurry as an isolated enzyme solution. For example, an α-amylase can be added in the form of a cultured cell material produced by host cells expressing an amylase. An α-amylase may also be secreted by a host cell into the reaction medium during the fermentation or SSF process, such that the enzyme is provided continuously into the reaction. The host cell producing and secreting amylase may also express an additional enzyme, such as a glucoamylase. For example, U.S. Pat. No. 5,422,267 discloses the use of a glucoamylase in yeast for production of alcoholic beverages. For example, a host cell, e.g., Trichoderma reesei or Aspergillus niger, may be engineered to co-express an α-amylase and a glucoamylase, e.g., HgGA, TrGA, or a TrGA variant, during saccharification. The host cell can be genetically modified so as not to express its endogenous glucoamylase and/or other enzymes, proteins or other materials. The host cell can be engineered to express a broad spectrum of various saccharolytic enzymes. For example, the recombinant yeast host cell can comprise nucleic acids encoding a glucoamylase, an alpha-glucosidase, an enzyme that utilizes pentose sugar, an α-amylase, a pullulanase, an isoamylase, and/or an isopullulanase. See, e.g., WO 2011/153516 A2.

4.4. Isomerization

The soluble starch hydrolysate produced by treatment with amylase can be converted into high fructose starch-based syrup (HFSS), such as high fructose corn syrup (HFCS). This conversion can be achieved using a glucose isomerase, particularly a glucose isomerase immobilized on a solid support. The pH is increased to about 6.0 to about 8.0, e.g., pH 7.5 (depending on the isomerase), and $Ca^{2+}$ is removed by ion exchange. Suitable isomerases include SWEETZYME®, IT (Novozymes A/S); G-ZYME® IMGI, and G-ZYME® G993, KETOMAX®, G-ZYME® G993, G-ZYME® G993 liquid, and GENSWEET® IGI. Following isomerization, the mixture typically contains about 40-45% fructose, e.g., 42% fructose.

4.5. Fermentation

The soluble starch hydrolysate, particularly a glucose rich syrup, can be fermented by contacting the starch hydrolysate with a fermenting organism typically at a temperature around 32° C., such as from 30° C. to 35° C. for alcohol-producing yeast. The temperature and pH of the fermentation will depend upon the fermenting organism. EOF products include metabolites, such as citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine and other amino acids, omega 3 fatty acid, butanol, isoprene, 1,3-propanediol and other biomaterials.

Ethanologenic microorganisms include yeast, such as Saccharomyces cerevisiae and bacteria, e.g., Zymomonas moblis, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) Sheng Wu Gong Cheng Xue Bao 27: 1049-56. Commercial sources of yeast include ETHANOL RED® (LeSaffre); FERMAX™ (Martrex), THERMO-SACC® (Lallemand); RED STAR® (Red Star); FER-MIOL® (DSM Specialties); and SUPERSTART® (Alltech). Microorganisms that produce other metabolites, such as citric acid and lactic acid, by fermentation are also known in the art. See, e.g., Papagianni (2007) Biotechnol. Adv. 25: 244-63; John et al. (2009) Biotechnol. Adv. 27: 145-52.

The saccharification and fermentation processes may be carried out as an SSF process. Fermentation may comprise subsequent enrichment, purification, and recovery of ethanol, for example. During the fermentation, the ethanol content of the broth or "beer" may reach about 8-18% v/v, e.g., 14-15% v/v. The broth may be distilled to produce enriched, e.g., 96% pure, solutions of ethanol. Further, $CO_2$ generated by fermentation may be collected with a $CO_2$ scrubber, compressed, and marketed for other uses, e.g., carbonating beverage or dry ice production. Solid waste from the fermentation process may be used as protein-rich products, e.g., livestock feed.

As mentioned above, an SSF process can be conducted with fungal cells that express and secrete amylase continuously throughout SSF. The fungal cells expressing amylase also can be the fermenting microorganism, e.g., an ethanologenic microorganism. Ethanol production thus can be carried out using a fungal cell that expresses sufficient amylase so that less or no enzyme has to be added exogenously. The fungal host cell can be from an appropriately engineered fungal strain. Fungal host cells that express and secrete other enzymes, in addition to amylase, also can be used. Such cells may express glucoamylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzyme.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, a limiting nutrient such as the carbon source or nitrogen source is maintained at a fixed rate and all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

4.6. Compositions Comprising Variants Amylases

Variant amylases may be combined with a glucoamylase (EC 3.2.1.3), e.g., a *Trichoderma* glucoamylase or variant thereof. An exemplary glucoamylase is *Trichoderma reesei* glucoamylase (TrGA) and variants thereof that possess superior specific activity and thermal stability. See U.S. Published Applications Nos. 2006/0094080, 2007/0004018, and 2007/0015266 (Danisco US Inc.). Suitable variants of TrGA include those with glucoamylase activity and at least 80%, at least 90%, or at least 95% sequence identity to wild-type TrGA. Variant amylases advantageously increase the yield of glucose produced in a saccharification process catalyzed by TrGA.

Alternatively, the glucoamylase may be *Aspergillus, Talaromyces, Clostridium, Fusarium, Thielavia, Thermomyces, Athelia, Humicola, Penicillium, Artomyces, Gloeophyllum, Pycnoporus, Steccherinum, Trametes* etc. Suitable commercial glucoamylases, include AMG 200L; AMG 300 L; SAN™ SUPER and AMG™ E (Novozymes); OPTIDEX® 300 and OPTIDEX L-400 (Danisco US Inc.); AMIGASE™ and AMIGASE™ PLUS (DSM); G-ZYME® G900 (Enzyme Bio-Systems); and G-ZYME® G990 ZR. Glucoamylases typically are added in an amount of about 0.1-2 glucoamylase units (GAU)/g ds, e.g., about 0.16 GAU/g ds, 0.23 GAU/g ds, or 0.33 GAU/g ds.

Other suitable enzymes that can be used with amylase include phytase, protease, pullulanase, β-amylase, isoamylase, α-glucosidase, cellulase, xylanase, other hemicellulases, 0-glucosidase, transferase, pectinase, lipase, cutinase, esterase, redox enzymes, a different α-amylase, or a combination thereof.

Compositions comprising the present amylases may be aqueous or non-aqueous formulations, granules, powders, gels, slurries, pastes, etc., which may further comprise any one or more of the additional enzymes listed, herein, along with buffers, salts, preservatives, water, co-solvents, surfactants, and the like. Such compositions may work in combination with endogenous enzymes or other ingredients already present in a slurry, water bath, washing machine, food or drink product, etc., for example, endogenous plant (including algal) enzymes, residual enzymes from a prior processing step, and the like.

5. Compositions and Methods for Baking and Food Preparation

The present invention also relates to a "food composition," including but not limited to a food product, animal feed and/or food/feed additives, comprising an amylase, and methods for preparing such a food composition comprising mixing variant amylase with one or more food ingredients, or uses thereof.

Furthermore, the present invention relates to the use of an amylase in the preparation of a food composition, wherein the food composition is baked subsequent to the addition of the polypeptide of the invention. As used herein the term "baking composition" means any composition and/or additive prepared in the process of providing a baked food product, including but not limited to baker's flour, a dough, a baking additive and/or a baked product. The food composition or additive may be liquid or solid.

6. Textile Desizing Compositions and Use

Also contemplated are compositions and methods of treating fabrics (e.g., to desize a textile) using an amylase. Fabric-treating methods are well known in the art (see, e.g., U.S. Pat. No. 6,077,316). For example, the feel and appearance of a fabric can be improved by a method comprising contacting the fabric with an amylase in a solution. The fabric can be treated with the solution under pressure.

An amylase can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An amylase can be applied during or after the weaving to remove these sizing starch or starch derivatives. After weaving, an amylase can be used to remove the size coating before further processing the fabric to ensure a homogeneous and wash-proof result.

An amylase can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. An amylase can be used in methods of finishing denim garments (e.g., a "bio-stoning process"), enzymatic desizing and providing softness to fabrics, and/or finishing process.

7. Cleaning Compositions

An aspect of the present compositions and methods is a cleaning composition that includes an amylase as a component. An amylase polypeptide can be used as a component in detergent compositions for, e.g., hand washing, laundry washing, dishwashing, and other hard-surface cleaning. Such compositions include heavy duty liquid (HDL), heavy duty dry (HDD), and hand (manual) laundry detergent compositions, including unit dose format laundry detergent compositions, and automatic dishwashing (ADW) and hand (manual) dishwashing compositions, including unit dose format dishwashing compositions.

7.1. Overview

Preferably, an amylase is incorporated into detergents at or near a concentration conventionally used for amylase in detergents. For example, an amylase polypeptide may be added in amount corresponding to 0.00001-1 mg (calculated as pure enzyme protein) of amylase per liter of wash/dishwash liquor. Exemplary formulations are provided herein, as exemplified by the following:

An amylase polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids.

The detergent composition may be in any useful form, e.g., as powders, granules, pastes, bars, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically amylases, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0, although mildly acidic conditions are not uncommon.

Particular forms of detergent compositions for inclusion of the present α-amylase are described, below. Many of these composition can be provided in unit dose format for ease of use. Unit dose formulations and packaging are described in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1.

7.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a C8-C18 alkyl ethoxylated alcohol and/or C6-C12 alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulphobetaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and copolymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition may further include saturated or unsaturated fatty acid, preferably saturated or unsaturated C12-C24 fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally includes silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

7.3. Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted C8-C18 alkyl ethoxylates, and/or C6-C12 alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C.I. Fluorescent brighteners), flocculating agents, chelating agents, alkoxylated polyamines, fabric deposition aids, and/or cyclodextrin.

7.4. Automatic Dishwashing (ADW) Detergent Composition

Exemplary ADW detergent composition includes non-ionic surfactants, including ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-poylphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

7.5. Additional Detergent Compositions

Additional exemplary detergent formulations to which the present amylase can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., C12-18 alcohol, 1-2 ethylene oxide (EO)) or alkyl sulfate (e.g., C16-18) about 1% to about 4%; alcohol ethoxylate (e.g., C14-15 alcohol, 7 EO) about 5% to about 9%; sodium carbonate about 14% to about 20%; soluble silicate about 2 to about 6%; zeolite about 15% to about 22%; sodium sulfate 0% to about 6%; sodium citrate/citric acid 0% to about 15%; sodium perborate about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., C12-18 alcohol, 1-2 EO) or alkyl sulfate (e.g., C16-18) about 1% to about 3%; alcohol ethoxylate (e.g., C14-15 alcohol, 7 EO) about 5% to about 9%; sodium carbonate about 15% to about 21%; soluble silicate about 1% to about 4%; zeolite about 24% to about 34%; sodium sulfate (e.g., $Na_2SO_4$) about 4% to about 10%; sodium citrate/citric acid 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., C12-15 alcohol, 7 EO) about 7% to about 14%; Soap as fatty acid (e.g., C16-22 fatty acid) about 1 to about 3%; sodium carbonate about 10% to about 17%; soluble silicate about 3% to about 9%; zeolite about 23% to about 33%; sodium sulfate 0% to about 4%; sodium perborate about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., C12-15 alcohol, 7 EO) about 10% to about 25%; sodium carbonate about 14% to about 22%; soluble silicate about 1% to about 5%; zeolite about 25% to about 35%; sodium sulfate 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., C12-15 alcohol, 7 EO or C12-15 alcohol, 5 EO) about 12% to about 18%; soap as fatty acid (e.g., oleic acid) about 3% to about 13%; alkenylsuccinic acid (C12-14) 0% to about 13%; aminoethanol about 8% to about 18%; citric acid about 2% to about 8%; phosphonate 0% to about 3%; polymers (e.g., PVP, PEG) 0% to about 3%; borate 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., C12-15 alcohol, 7 EO, or C12-15 alcohol, 5 EO) 3-9%; soap as fatty acid (e.g., oleic acid) about 3% to about 10%; zeolite about 14% to about 22%; potassium citrate about 9% to about 18%; borate 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate about 5% to about 10%; Soluble silicate about 1% to about 4%; zeolite about 20% to about 40%; Sodium sulfate about 2% to about 8%; sodium perborate about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate about 4% to about 10%; soluble silicate about 1% to about 4%; zeolite about 30% to about 50%; sodium sulfate about 3% to about 11%; sodium citrate about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate about 14% to about 22%; zeolite about 18% to about 32%; sodium sulfate about 5% to about 20%; sodium citrate about 3% to about 8%; sodium perborate about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., C12-15 alcohol, 2-3 EO) about 8% to about 15%; alcohol ethoxylate (e.g., C12-15 alcohol, 7 EO, or C12-15 alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., C12-15 alcohol, 7 EO, or C12-15 alcohol, 5 EO) 6-12%; aminoethanol about 2% to about 6%; citric acid about 8% to about 14%; borate about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate about 8% to about 25%; soluble silicates about 5% to about 15%; sodium sulfate 0% to about 5%; zeolite about 15% to about 28%; sodium perborate 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by (C12-C18) alkyl sulfate.

14) A detergent composition formulated as a granulate having a bulk density of at least 600 g/L comprising (C12-C18) alkyl sulfate about 9% to about 15%; alcohol ethoxylate about 3% to about 6%; polyhydroxy alkyl fatty acid amide about 1% to about 5%; zeolite about 10% to about 20%; layered disilicate (e.g., SK56 from Hoechst) about 10% to about 20%; sodium carbonate about 3% to about 12%; soluble silicate 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising (C12-C18) alkyl sulfate about 4% to about 8%; alcohol ethoxylate about 11% to about 15%; soap about 1% to about 4%; zeolite MAP or zeolite A about 35% to about 45%; sodium carbonate about 2% to about 8%; soluble silicate 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described by Hage et al. ((1994) *Nature* 369: 637-639).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present amylase polypeptide may be incorporated at a concentration conventionally employed in detergents. It is at present contemplated that, in the detergent composition, the enzyme may be added in an amount corresponding to 0.00001-1.0 mg (calculated as pure enzyme protein) of amylase polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general, the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases: Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Exemplary proteases include but are not limited to those described in WO95/23221, WO 92/21760, WO2008010925, WO20100566356, WO2011072099, WO201113022, WO2011140364, WO 2012151534, WO2015038792, WO2015089441, WO2015089447, WO2015143360, WO2016001449, WO2016001450, WO2016061438, WO2016069544, WO2016069548, WO2016069552, WO 2016069557, WO2016069563, WO2016069569, WO2016087617, WO2016087619, WO2016145428, WO2016174234, WO2016183509, WO2016202835, WO2016205755, US 2008/0090747, U.S. Pat. Nos. 5,801,039, 5,340,735, 5,500,364, 5,855,625, RE 34,606, U.S. Pat. Nos. 5,955,340, 5,700,676, 6,312,936, 6,482,628, 8,530,219, U.S. Provisional Appl Nos. 62/331, 282, 62/343,618, 62/351,649, 62/437,171, 62/437,174, and 62/437,509, and PCT Appl Nos. PCT/CN2017/076749 and, as well as metalloproteases described in WO 2007/044993, WO 2009/058303, WO 2009/058661, WO 2014/071410, WO 2014/194032, WO 2014/194034, WO 2014/194054, and WO 2014/194117.

Exemplary commercial proteases include, but are not limited to MAXATASE, MAXACAL, MAXAPEM, OPTI-CLEAN®, OPTIMASE®, PROPERASE®, PURAFECT®, PURAFECT® OXP, PURAMAX®, EXCELLASE®, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST (Danisco US); ALCALASE®, ALCALASE® ULTRA, BLAZE®, BLAZE® EVITY®, BLAZE® EVITY® 16L, CORONASE®, SAVINASE®, SAVINASE® ULTRA, SAVINASE® EVITY®, SAVINASE® EVERTS®, PRIMASE, DURAZYM, POLARZYME®, OVOZYME®, KANNASE®, LIQUANASE®, EVERTS®, NEUTRASE®, PROGRESS UNO®, RELASE® and ESPERASE® (Novozymes); BLAP™ and BLAP™ variants (Henkel); LAVERGY™ PRO 104 L (BASF), and KAP® (*B. alkalophilus* subtilisin) (Kao). Suitable proteases include naturally occurring proteases or engineered variants specifically selected or engineered to work at relatively low temperatures.

Lipases: Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (T *lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens, Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. (1993) *Biochemica et Biophysica Acta* 1131:253-360), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105.

Exemplary commercial lipases include, but are not limited to M1 LIPASE, LUMA FAST, and LIPOMAX (Genencor); LIPEX®, LIPOCLEAN®, LIPOLASE® and LIPOLASE® ULTRA (Novozymes); and LIPASE P (Amano Pharmaceutical Co. Ltd).

Polyesterases: Suitable polyesterases can be included in the composition, such as those described in, for example, WO 01/34899, WO 01/14629, and U.S. Pat. No. 6,933,140.

Amylases: The present compositions can be combined with other amylases, including other α-amylases. Such a combination is particularly desirable when different α-amylases demonstrate different performance characteristics and the combination of a plurality of different α-amylases results in a composition that provides the benefits of the different α-amylases. Other amylases include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, PURASTAR®, and PREFERENZ™ (from DuPont Industrial Biosciences.). Exemplary α-amylases are described in WO9418314A1, US20080293607, WO2013063460, WO10115028, WO2009061380A2, WO2014099523, WO2015077126A1, WO2013184577, WO2014164777, WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO2006002643, WO2004055178, and WO9813481.

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Exemplary cellulases include those described in WO2005054475, WO2005056787, U.S. Pat. Nos. 7,449,318, 7,833,773, 4,435,307; EP 0495257; and U.S. Provisional Appl. Nos. 62/296,678 and 62/435,340. Exemplary commercial cellulases include, but are not limited to, CELLUCLEAN®, CELLUZYME®, CAREZYME®, CAREZYME® PREMIUM, ENDOLASE®, and RENOZYME® (Novozymes); REVITALENZ®100, REVITALENZ® 200/220 and REVITALENZ® 2000 (Danisco US); and KAC-500(B) (Kao Corporation).

Mannanases: Exemplary mannanases include, but are not limited to, those of bacterial or fungal origin, such as, for example, as is described in WO2016007929; U.S. Pat. Nos. 6,566,114, 6,602,842, and 6,440,991; and International Appl Nos. PCT/US2016/060850 and PCT/US2016/060844. Exemplary mannanases include, but are not limited to, those of bacterial or fungal origin, such as, for example, as is described in WO2016007929; U.S. Pat. Nos. 6,566,114, 6,602,842, and 6,440,991; and International Appl Nos. PCT/US2016/060850 and PCT/US2016/060844.

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated, e.g., as a granulate, a liquid, a slurry, and the like. Exemplary detergent additive formulations include but are not limited to granulates, in particular non-dusting granulates, liquids, in particular stabilized liquids or slurries.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates, e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Numerous exemplary detergent formulations to which the present amylases can be added (or is in some cases are identified as a component of) are described in WO2013063460. These include commercially available unit dose detergent formulations/packages such as PUREX® UltraPacks (Henkel), FINISH® Quantum (Reckitt Benckiser), CLOROX™ 2 Packs (Clorox), OxiClean Max Force Power Paks (Church & Dwight), TIDE® Stain Release, CASCADE® ActionPacs, and TIDE® Pods (Procter & Gamble), PS.

7.6. Methods of Assessing Amylase Activity in Detergent Compositions

Numerous α-amylase cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

8. Brewing Compositions

The present variant amylase may be a component of a brewing composition used in a process of brewing, i.e., making a fermented malt beverage. Non-fermentable carbohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces of beer. An amylase, in combination with a glucoamylase and optionally a pullulanase and/or isoamylase, assists in converting the starch into dextrins and fermentable sugars, lowering the residual non-fermentable carbohydrates in the final beer.

All references cited herein are herein incorporated by reference in their entirety for all purposes. In order to further illustrate the compositions and methods, and advantages thereof, the following specific examples are given with the understanding that they are illustrative rather than limiting.

EXAMPLE

Example 1: Preparation of Variant Amylases

DNA sequences encoding variant α-amylases, a signal peptide for secretion, and additional 5' and 3' sequences for amplification and subcloning were constructed by standard PCR amplification or ordered from a commercial vendor (GeneArt). Standard procedures were used to insert the DNA sequence into a bacterial vector for secreted protein expression in *Bacillus subtilis* cells. The constructs were verified by DNA sequencing. Cells were grown for about 68 hours in expression medium suitable for secreted protein expression from *B. subtilis*. Cells were separated from protein-containing supernatant by centrifugation followed by filtration through 0.45 μm membranes (EMD Millipore). When needed, additional purification was achieved through ion exchange chromatography with Phenyl Sepharose 6 Fast Flow resin (GE Healthcare). Protein concentration was determined by high performance liquid chromatography (HPLC) and absorbance at 280 nm.

Example 2: Starch Cleaning Activity in CS28 Microswatch Assay

Starch cleaning activity of variant α-amylases was evaluated with rice starch on cotton commercial test fabric (CS28, Center for Test Materials, Netherlands) cut to 5.5 mm circular swatches. Two swatches were placed in each well of a 96-well Corning 9017 flat-bottomed polystyrene microtiter plate. Solutions of protein in buffer (50 mM CAPS, 1 mM $CaCl_2$, 0.005% Tween-80 v/v, pH 10.5), diluted from the original supernatant, were added to the test fabric. The solution was shaken for 15 minutes at 23° C. Samples of the supernatant were evaluated for release of dye by measuring the absorbance of the solution at 488 nm with a spectrophotometer. The standard curve was fit to an exponential reaction progress curve and the samples of the variant were similarly fit using fixed initial and end absorbances. The performance index was defined as the ratio of the exponential fit constant for the variant relative to that of a standard curve based on the results obtained with CspAmy2-v1 (SEQ ID NO: 2 in WO2014/164777 and US20160017303A1). STAINZYME® 12L (SEQ ID NO: 1 in WO2017114891) was included as a commercial benchmark. STAINZYME® 12L is a variant of the α-amylase from *Bacillus* sp. AA560 (present SEQ ID NO: 7 and SEQ ID NO: 2 in WO2017114891). The results are shown in Table 1.

TABLE 1

Cleaning performance of α-amylase variants

| Amylase | Performance Index |
|---|---|
| Amy707-3790H | 4.5 |
| Amy707-2170D | 4.8 |
| Amy707-3156D | 4.5 |
| Amy707-3915D | 4.8 |
| Amy707-4037D | 2.8 |
| STAINZYME ® 12L | 3.7 |
| CspAmy2-v1 | (1) |

Amy707-3790H, Amy707-2170D, Amy707-3156D and Amy707-3915D clearly outperformed both CspAmy2-v1 and STAINZYME® 12L. Amy707-4037D outperformed CspAmy2-v1.

Example 3: Stability of the Variants

The relative stability of the α-amylase variants was evaluated by measuring the loss of activity upon incubation in buffer (50 mM CAPS, 2 mM $CaCl_2$, 0.005% Tween-80 v/v, pH 10.5) at an elevated temperature. Solutions of the enzyme in buffer were stressed at 85° C. for 15 minutes in a thermocycler. Samples of enzyme in the test solutions were taken both before and after stressing the solution at elevated temperature. Amylase activity present in the samples was evaluated using the Amylase HR assay (Megazyme). The results are shown in Table 2.

TABLE 2

Stability of α-amylase variants

| Amylase | Residual Activity |
| --- | --- |
| Amy707-3790H | 68% |
| Amy707-2170D | 46% |
| Amy707-3156D | 15% |
| Amy707-3915D | 3% |
| Amy707-4037D | 3% |
| STAINZYME ® 12L | 2% |
| CspAmy2-v1 | 33% |

Amy707-3790H and Amy707-2170D clearly outperformed CspAmy2-v1, while all variants outperformed STAINZYME® 12L.

All publications, patents, and patent applications cited herein are hereby incorporated by reference in their entireties for all purposes and to the same extent as if each individual publication, patent, or patent application were specifically and individually indicated to be so incorporated by reference.

What is claimed is:

1. A recombinant variant α-amylase comprising an amino acid sequence having at least 97% amino acid sequence identity to the amino acid sequence of SEQ ID NO: 2, excluding the wild-type Amy707 enzyme having the amino acid sequence of SEQ ID NO: 2.

2. A composition for liquefying starch comprising the variant α-amylase of claim 1.

3. A detergent composition comprising the variant α-amylase of claim 1.

* * * * *

```
SEQUENCE LISTING

<160> NUMBER OF SEQ ID NOS: 12

<210> SEQ ID NO 1
<211> LENGTH: 485
<212> TYPE: PRT
<213> ORGANISM: Bacillus sp. 707

<400> SEQUENCE: 1

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190
```

```
Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 2
<211> LENGTH: 483
<212> TYPE: PRT
<213> ORGANISM: Artificial
<220> FEATURE:
<223> OTHER INFORMATION: Variant of Amy707 alpha-amylase

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Tyr
        35                  40                  45

Lys Gly Thr Ser Gln Asn Asp Val Gly Tyr Gly Ala Tyr Asp Leu Tyr
    50                  55                  60
```

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Ser Asn Arg Asn
            115                 120                 125

Gln Glu Ile Ser Gly Asp Tyr Thr Ile Glu Ala Trp Thr Lys Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe His Gly Lys Ala Trp Asp Trp Pro Val Ser Ser Glu
            180                 185                 190

Asn Gly Asn Tyr Asp Tyr Leu Met Tyr Ala Asp Ile Asp Met Asp His
            195                 200                 205

Pro Asp Val Val Asn Glu Leu Arg Asn Trp Gly Val Trp Tyr Ala Asn
210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
            275                 280                 285

Val Pro Leu His Tyr Asn Leu Tyr Asn Ala Ser Lys Ser Gly Gly Asn
290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
            355                 360                 365

Tyr Tyr Gly Ile Pro Thr His Gly Val Pro Ala Met Arg Ser Lys Ile
370                 375                 380

Asp Pro Ile Leu Glu Ala Arg Gln Lys Tyr Ala Tyr Gly Lys Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
            420                 425                 430

Gly Gly Ser Lys Trp Met Asn Val Gly Lys Asn Asn Ala Gly Glu Val
            435                 440                 445

Trp Tyr Asp Ile Thr Gly Asn Arg Thr Gly Thr Val Thr Ile Asn Ala
            450                 455                 460

Asp Gly Trp Gly Gln Phe His Val Asn Gly Gly Ser Val Ser Ile Trp
465                 470                 475                 480

Val Asn Lys

```
<210> SEQ ID NO 3
<211> LENGTH: 483
<212> TYPE: PRT
<213> ORGANISM: Artificial
<220> FEATURE:
<223> OTHER INFORMATION: Variant of Amy707 alpha-amylase

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Tyr Thr Glu Thr Val Thr Ala Val Glu Val Asn Pro Asn Asn Arg Asn
        115                 120                 125

Gln Glu Thr Ser Gly Glu Tyr Asn Ile Gln Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Asp Gly Lys Ala Trp Asp Trp Pro Val Ser Ser Glu
            180                 185                 190

Asn Gly Asn Tyr Asp Tyr Leu Met Tyr Ala Asp Val Asp Phe Glu His
        195                 200                 205

Pro Glu Val Val Asn Glu Met Lys Lys Trp Gly Val Trp Tyr Thr Asn
210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365
```

-continued

```
Tyr Tyr Gly Ile Pro Thr His Gly Val Pro Ala Met Arg Ser Lys Ile
    370                 375                 380

Asp Pro Ile Leu Glu Ala Arg Gln Lys Tyr Ala Tyr Gly Lys Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Leu Ile Ser Asp Gly Pro
            420                 425                 430

Gly Gly Ser Lys Trp Met Phe Val Gly Arg Asn Lys Ala Gly Gln Val
        435                 440                 445

Trp Ser Asp Ile Thr Gly Asn Arg Thr Gly Thr Val Thr Ile Asn Ala
450                 455                 460

Asp Gly Trp Gly Asn Phe Ser Val Asn Gly Gly Ser Val Ser Ile Trp
465                 470                 475                 480

Val Asn Lys

<210> SEQ ID NO 4
<211> LENGTH: 483
<212> TYPE: PRT
<213> ORGANISM: Artificial
<220> FEATURE:
<223> OTHER INFORMATION: Variant of Amy707 alpha-amylase

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Asp Gly Lys Ala Trp Asp Trp Pro Val Ser Ser Glu
            180                 185                 190

Asn Gly Asn Tyr Asp Tyr Leu Met Tyr Ala Asp Leu Asp Phe Asp His
        195                 200                 205

Pro Asp Val Ala Asn Glu Met Lys Asn Trp Gly Thr Trp Tyr Ala Asn
    210                 215                 220

Glu Leu Asn Leu Asp Gly Phe Arg Leu Asp Ala Val Lys His Ile Asp
225                 230                 235                 240
```

```
His Glu Tyr Leu Arg Asp Trp Val Asn His Val Arg Gln Gln Thr Gly
            245                 250                 255

Lys Asn Met Phe Ala Val Ala Glu Phe Trp Lys Asn Asp Leu Gly Ala
        260                 265                 270

Ile Glu Asn Tyr Leu Gln Lys Thr Asn Trp Asn Gln Ser Val Phe Asp
        275                 280                 285

Ala Pro Leu His Tyr Asn Leu Tyr Asn Ala Ser Lys Ser Gly Gly Asn
        290                 295                 300

Tyr Asp Met Arg Asn Ile Phe Asn Gly Thr Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Glu Gln Gly Tyr Pro Ser Val Phe Tyr Gly Asp
            355                 360                 365

Tyr Tyr Gly Ile Pro Thr His Gly Val Pro Ala Met Arg Ser Lys Ile
        370                 375                 380

Asp Pro Ile Leu Glu Ala Arg Gln Lys Tyr Ala Tyr Gly Lys Gln Asn
385                 390                 395                 400

Asp Tyr Leu Asp His His Asn Ile Ile Gly Trp Thr Arg Glu Gly Asp
                405                 410                 415

Ser Thr Lys Ala Asn Ser Gly Leu Ala Thr Ile Met Ser Asp Gly Pro
            420                 425                 430

Gly Gly Ser Lys Trp Met Asn Val Gly Lys Gln Asn Ala Gly Glu Val
            435                 440                 445

Trp Tyr Asp Ile Thr Gly Asn Arg Thr Gly Thr Val Thr Ile Asn Ser
        450                 455                 460

Asp Gly Trp Gly Gln Phe Phe Val Asn Gly Gly Ser Val Ser Ile Trp
465                 470                 475                 480

Val Asn Lys

<210> SEQ ID NO 5
<211> LENGTH: 483
<212> TYPE: PRT
<213> ORGANISM: Artificial
<220> FEATURE:
<223> OTHER INFORMATION: Variant of Amy707 alpha-amylase

<400> SEQUENCE: 5

His His Asn Gly Thr Asn Gly Thr Leu Met Gln Tyr Phe Glu Trp Tyr
1               5                   10                  15

Ala Pro Asn Asp Gly Gln His Trp Asn Arg Leu Arg Ser Asp Ala Glu
            20                  25                  30

Asn Leu Ala Gln Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Gln Leu Lys Ser Ala Val Thr Ser Leu Lys Asn Asn Gly
                85                  90                  95

Ile Gln Val Tyr Gly Asp Val Val Met Asn His Lys Gly Gly Ala Asp
            100                 105                 110
```

Ala Thr Glu Thr Val Thr Ala Val Glu Val Asn Pro Ser Asn Arg Asn
115                 120                 125

Gln Glu Thr Ser Gly Glu Tyr Asn Ile Gln Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Thr Asp Trp Asp Gln Ser Arg Arg Leu Asn Asn Arg
            165                 170                 175

Ile Tyr Lys Phe Asp Gly Lys Ala Trp Asp Trp Pro Val Ser Ser Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
            245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
            275                 280                 285

Val Pro Leu His Tyr Asn Leu Tyr Asn Ala Ser Lys Ser Gly Gly Asn
            290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
            325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
            355                 360                 365

Tyr Tyr Gly Ile Pro Thr His Gly Val Pro Ala Met Arg Ser Lys Ile
370                 375                 380

Asp Pro Ile Leu Glu Ala Arg Gln Lys Tyr Ala Tyr Gly Lys Gln Asn
385                 390                 395                 400

Asp Tyr Leu Asp His His Asn Ile Ile Gly Trp Thr Arg Glu Gly Asp
            405                 410                 415

Ser Thr Lys Ala Asn Ser Gly Leu Ala Thr Ile Met Ser Asp Gly Pro
            420                 425                 430

Gly Gly Ser Lys Trp Met Asn Val Gly Lys Asn Asn Ala Gly Gln Val
            435                 440                 445

Trp Ser Asp Ile Thr Gly Asn Arg Thr Gly Thr Val Thr Ile Asn Ala
450                 455                 460

Asp Gly Trp Gly Gln Phe Phe Val Asn Gly Gly Ser Val Ser Ile Trp
465                 470                 475                 480

Val Asn Lys

<210> SEQ ID NO 6
<211> LENGTH: 482
<212> TYPE: PRT
<213> ORGANISM: Artificial
<220> FEATURE:
<223> OTHER INFORMATION: Variant of Amy707 alpha-amylase

<400> SEQUENCE: 6

```
Ala Thr Val Asn Asn Gly Thr Leu Met Gln Tyr Phe Glu Trp Tyr Leu
  1               5                  10                  15

Pro Asn Asp Gly Gln His Trp Asn Arg Leu Asn Ser Asp Ala Ser Asn
             20                  25                  30

Leu Lys Ser Lys Gly Ile Thr Ala Val Trp Ile Pro Pro Ala Tyr Lys
         35                  40                  45

Gly Thr Thr Gln Asn Asp Val Gly Tyr Gly Ala Tyr Asp Leu Tyr Asp
     50                  55                  60

Leu Gly Glu Phe Asn Gln Lys Gly Thr Val Arg Thr Lys Tyr Gly Thr
 65                  70                  75                  80

Arg Ser Gln Leu Gln Ala Ala Val Thr Ser Leu Lys Asn Asn Gly Ile
                 85                  90                  95

Gln Val Tyr Gly Asp Ala Val Met Asn His Lys Gly Ala Asp Ala
             100                 105                 110

Thr Glu Met Val Arg Ala Val Glu Val Asn Pro Ser Asn Arg Asn Gln
         115                 120                 125

Glu Thr Ser Gly Glu Tyr Asn Ile Gln Ala Trp Thr Gly Phe Asn Phe
     130                 135                 140

Pro Gly Arg Gly Asn Thr His Ser Ser Phe Lys Trp Arg Trp Tyr His
145                 150                 155                 160

Phe Asp Gly Val Asp Trp Asp Gln Ser Arg Arg Leu Asn Asn Arg Ile
                 165                 170                 175

Tyr Lys Phe Asp Gly Lys Ala Trp Asp Trp Pro Val Ser Ser Glu Asn
             180                 185                 190

Gly Asn Tyr Asp Tyr Leu Met Tyr Ala Asp Leu Asp Phe Asp His Pro
         195                 200                 205

Asp Val Val Asn Glu Met Lys Glu Trp Gly Val Trp Tyr Ala Asn Thr
     210                 215                 220

Leu Gly Leu Asp Gly Phe Arg Ile Asp Ala Val Lys His Ile Lys Tyr
225                 230                 235                 240

Ser Phe Thr Arg Asp Trp Ile Asn His Val Arg Ser Ala Thr Gly Lys
                 245                 250                 255

Asn Met Phe Ala Val Ala Glu Phe Trp Lys Asn Asp Leu Gly Ala Ile
             260                 265                 270

Glu Asn Tyr Leu Gln Lys Thr Asn Trp Asn His Ser Val Phe Asp Val
         275                 280                 285

Pro Leu His Tyr Asn Leu Tyr Asn Ala Ser Lys Ser Gly Gly Asn Tyr
     290                 295                 300

Asp Met Arg Asn Ile Phe Asn Gly Thr Val Val Gln Arg His Pro Ser
305                 310                 315                 320

His Ala Val Thr Phe Val Asp Asn His Asp Ser Gln Pro Glu Glu Ala
                 325                 330                 335

Leu Glu Ser Phe Val Glu Glu Trp Phe Lys Pro Leu Ala Tyr Ala Leu
             340                 345                 350

Thr Leu Thr Arg Glu Gln Gly Tyr Pro Ser Val Phe Tyr Gly Asp Tyr
         355                 360                 365

Tyr Gly Ile Pro Thr His Gly Val Pro Ala Met Arg Ser Lys Ile Asp
     370                 375                 380

Pro Ile Leu Glu Ala Arg Gln Lys Tyr Ala Tyr Gly Lys Gln Asn Asp
385                 390                 395                 400

Tyr Leu Asp His His Asn Ile Ile Gly Trp Thr Arg Glu Gly Asn Thr
                 405                 410                 415
```

```
Ala His Pro Asn Ser Gly Leu Ala Thr Ile Met Ser Asp Gly Pro Gly
            420                 425                 430

Gly Ser Lys Trp Met Phe Val Gly Arg Asn Lys Ala Gly Gln Val Trp
            435                 440                 445

Ser Asp Ile Thr Gly Asn Arg Thr Gly Thr Val Thr Ile Asn Ala Asp
            450                 455                 460

Gly Trp Gly Asn Phe Ser Val Asn Gly Ser Val Ser Ile Trp Val
465                 470                 475                 480

Asn Lys

<210> SEQ ID NO 7
<211> LENGTH: 485
<212> TYPE: PRT
<213> ORGANISM: Bacillus sp. AA560

<400> SEQUENCE: 7

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300
```

```
Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
            325                 330                 335

Glu Glu Ala Leu Glu Ser Phe Val Glu Glu Trp Phe Lys Pro Leu Ala
        340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 8
<211> LENGTH: 1452
<212> TYPE: DNA
<213> ORGANISM: Artificial
<220> FEATURE:
<223> OTHER INFORMATION: Coding sequence for Amy707 variant

<400> SEQUENCE: 8
catcataacg gtacaaacgg aacaatgatg cagtatttcg agtggtatct acctaacgac        60
ggcaatcatt ggaacagact gaactcagat gccagtaact tgaaatctaa aggtattaca       120
gcagtatgga ttccgccggc ttataagggc acgtctcaaa atgatgtggg gtacggcgca       180
tacgatctgt atgatttagg cgagtttaat caaaaaggta cagtcagaac gaagtatggc       240
acaagaagtc aacttcaagc cgctgttacc tcgctgaaaa ataatggaat ccaagtgtat       300
ggtgatgtcg tgatgaatca taaggaggt gctgatgcta cagaaatggt aagggcggtg       360
gaggtgaatc cgtctaatag aaatcaggaa attagcggcg attatacaat tgaagcatgg       420
acaaaattcg attttccggg ccgaggaaat acgcattcta gcttcaaatg gaggtggtac       480
cattttgatg gagtggattg ggaccagagc agaagactca acaatagaat ctacaaattc       540
catgaaaggg cgtgggactg gccggtttct tcagaaaacg gaaattatga ctatctgatg       600
tacgcggaca ttgatatgga ccatccggat gtcgtgaatg aattgagaaa ttggggcgtc       660
tggtatgcca acacattagg gttagatgga ttcagaattg acgcggtcaa acatattaaa       720
tatagcttta ccagagactg gattaatcac gtaagatcag cgacgggaaa aaatatgttt       780
gcggttgccg aattttggaa aaatgattta ggggccattg aaaactacct gcaaaagaca       840
aattggaacc attctgtttt tgatgtgccg ttgcattaca accttttacaa tgcctcaaaa       900 agcggtggaa attacgatat gagaaatatt tttaatggca cggtagtcca acgccatccg       960
agtcatgctg ttacgtttgt tgataatcat gactcacagc ctgaagaagc actggaatca      1020
```

```
tttgtcgaag agtggtttaa accgttagcc tatgcgctta ctctcacgag agaacaaggc    1080
tatccttctg tattttatgg agattattac ggtattccaa cacatggggt ccctgctatg    1140
agatctaaaa tcgatcctat tcttgaggct agacaaaagt atgcttatgg aaaacagaat    1200
gactatttag atcaccataa tatcattggc tggacgagag aagggaacac agcgcacccc    1260
aatagcggtc tggccacaat catgtcagat ggggcgggcg gttcaaaatg gatgaatgtt    1320
ggcaaaaata tgcgggtga agtttggtat gatattacag ggaatagaac aggtacagtc    1380
acgattaatg ccgatggctg gggccaattt catgtcaatg ggggctcagt ttcaatatgg    1440
gtgaacaaat ga                                                        1452

<210> SEQ ID NO 9
<211> LENGTH: 1452
<212> TYPE: DNA
<213> ORGANISM: Artificial
<220> FEATURE:
<223> OTHER INFORMATION: Coding sequence for Amy707 variant

<400> SEQUENCE: 9
catcataacg gtacgaacgg gacaatgatg caatactttg aatggtatct acctaatgac      60
ggaaatcatt ggaatcgatt aaactctgat gcgagtaacc ttaaaagcaa agggattaca    120
gcggtgtgga ttcctccagc atggaagggc gcttctcaaa atgacgtagg atacggagcc    180
tatgacctgt atgatctggg agaatttaat caaaaggta ccgtccgtac aaaatatgga     240
acacgtagtc agttacaagc tgcggtaacc tccttaaaaa ataatggaat tcaagtatat    300
ggtgacgttg ttatgaatca caaggtggc gcagactata ctgaaacagt aacggccgtt     360
gaagtgaatc ccaataaccg taaccaagaa acatctggtg aatataatat tcaagcttgg    420
actagatttg attttccagg cgaggaaat actcattcta gctttaaatg gagatggtat    480
cattttgatg gtgtggattg ggatcagtca cgtagactga acaatcgcat ctataaattt    540
gatggcaaag cttgggattg gccagttagt tctgaaaatg gtaattatga ttatttgatg    600
tacgctgatg ttgattttga acacccagaa gtagtaaatg aaatgaaaaa gtggggtgtt    660
tggtacacaa acacattagg actcgatgga tttagaatag atgcggttaa acatataaag    720
tatagcttta cgcgcgattg gattaatcac gttagaagtg caacaggtaa aaatatgttt    780
gcggttgctg agttttggaa gaatgattta ggtgcaattg aaaactatct gcagaaaaca    840
aactggaacc attcagtctt tgatgtgccg ttcattata atctgtataa tgcatcaaaa    900
agcggaggga actatgatat gcgaaacata tttaatggaa cggttgttca acgacatcca    960
agtcatgctg taacatttgt tgataatcat gattcgcagc ctgaagaagc attagaatct    1020
tttgttgaag aatggttaa accattagcg tatgcgctta cattaacgcg tgaacaagga    1080 taccttctg tattttacgg agattattat gggattccaa cacatggagt gccagcaatg    1140
agatcaaaaa tcgatccgat tttagaagca cgtcaaaagt atgcatacgg aaaacaaaat    1200
gattacttag accatcataa tatcattggt tggacgcgtg aagggaatac agcacacccc    1260
aattcaggtc tagctaccct aatttctgat ggaccaggtg aagtaagtg gatgtttgtt    1320 gggcgtaata aggctggtca agtatggagt gatattacag gaaaccgtac aggtacggtt    1380
acaatcaatg cagacggttg gggcaatttc tctgtgaatg gagggtcagt ttctattgg    1440 gtcaacaaat aa                                                        1452
```

<210> SEQ ID NO 10
<211> LENGTH: 1452
<212> TYPE: DNA
<213> ORGANISM: Artificial
<220> FEATURE:
<223> OTHER INFORMATION: Coding sequence for Amy707 variant

<400> SEQUENCE: 10

| | | | | | |
|---|---|---|---|---|---|
| catcataacg | gtacgaacgg | gacaatgatg | caatactttg | aatggtatct | acctaatgac | 60 |
| ggaaatcatt | ggaatcgatt | aaactctgat | gcgagtaacc | ttaaaagcaa | agggattaca | 120 |
| gcggtgtgga | ttcctccagc | atggaagggc | acatctcaaa | atgacgtagg | atacggagcc | 180 |
| tatgacctgt | atgatctggg | agaatttaat | caaaaaggta | ccgtccgtac | aaaatatgga | 240 |
| acacgtagtc | agttacaagc | tgcggtaacc | tccttaaaaa | ataatggaat | tcaagtatat | 300 |
| ggtgacgttt | tatgaatca | caaaggtggc | gcagacgcta | ctgaaatggt | aagggccgtt | 360 |
| gaagtgaatc | ccaataaccg | taaccaagaa | gtgactggtg | aatataccat | tgaagcttgg | 420 |
| actagatttg | attttccagg | gcgaggaaat | actcattcta | attttaaatg | gagatggtat | 480 |
| cattttgatg | gtgtggattg | ggatcagtca | cgtagactga | acaatcgcat | ctataaattt | 540 |
| gatggcaaag | cttgggattg | gccagtttca | tctgaaaatg | gtaattatga | ttatttgatg | 600 |
| tacgctgatt | tagattttga | tcacccagat | gtagcaaatg | aaatgaaaaa | ttggggtaca | 660 |
| tggtacgcaa | acgaattaaa | tctcgatgga | tttagattag | atgcggttaa | acatatagat | 720 |
| catgaatatt | tacgcgattg | ggttaatcac | gttagacaac | agacaggtaa | aaatatgttt | 780 |
| gcggttgctg | agttttggaa | gaatgattta | ggtgcaattg | aaaactatct | gcagaaaaca | 840 |
| aactggaacc | aatcagtctt | tgatgctccg | ttacattata | atctgtataa | tgcatcaaaa | 900 |
| agcggaggga | actatgatat | gcgaaacata | tttaatggaa | cggttgttca | acgacatcca | 960 |
| agtcatgctg | taacatttgt | tgataatcat | gattcgcagc | ctgaagaagc | attagaatct | 1020 |
| tttgttgaag | aatggtttaa | accattagcg | tatgcgctta | cattaacgcg | tgaacaagga | 1080 |
| tacccttctg | tattttacgg | agattattat | gggattccaa | cacatggagt | gccagcaatg | 1140 |
| agatcaaaaa | tcgatccgat | tttagaagca | cgtcaaaagt | atgcatacgg | aaaacaaaat | 1200 |
| gattacttag | accatcataa | tatcattggt | tggacgcgtg | aagggatag | tacaaaagca | 1260 |
| aattcaggtc | tagctaccat | catgtctgat | ggaccaggtg | gaagtaagtg | gatgaatgtt | 1320 |
| gggaaacaaa | atgctggtga | agtatggtat | gatattacag | gaaaccgtac | aggtacggtt | 1380 |
| acaatcaatt | ctgacggttg | gggccaattc | tttgtgaatg | gagggtcagt | ttctatttgg | 1440 |
| gtcaacaaat | aa | | | | | 1452 |

<210> SEQ ID NO 11
<211> LENGTH: 1452
<212> TYPE: DNA
<213> ORGANISM: Artificial
<220> FEATURE:
<223> OTHER INFORMATION: Coding sequence for Amy707 variant

<400> SEQUENCE: 11

| | | | | | |
|---|---|---|---|---|---|
| catcataacg | gtacgaacgg | gacattaatg | caatactttg | aatggtatgc | acctaatgac | 60 |
| ggacaacatt | ggaatcgatt | aagatctgat | gcggaaaacc | ttgcgcaaaa | agggattaca | 120 |
| gcggtgtgga | ttcctccagc | atggaagggc | gcttctcaaa | atgacgtagg | atacggagcc | 180 |
| tatgacctgt | atgatctggg | agaatttaat | caaaaaggta | ccgtccgtac | aaaatatgga | 240 |
| acaaaagcgc | agttaaaaag | tgcggtaacc | tccttaaaaa | ataatggaat | tcaagtatat | 300 |

```
ggtgacgttg ttatgaatca caaaggtggc gcagacgcta ctgaaacagt aacggccgtt      360
gaagtgaatc cctctaaccg taaccaagaa acatcaggtg aatataatat tcaagcttgg      420
actagatttg attttccagg gcgaggaaat actcattcta gctttaaatg gagatggtat      480
cattttgatg gtacagattg ggatcagtca cgtagactga acaatcgcat ctataaattt      540
gatggcaaag cttgggattg gccagttagt tctgaaaatg gtaattatga ttatttgatg      600
tacgctgata ttgatatgga tcacccagaa gtagtaaatg aattaagaaa ttggggtgtt      660
tggtacacaa acacattagg actcgatgga tttagaatag atgcggttaa acatataaag      720
tatagcttta cgcgcgattg gattaatcac gttagaagtg caacaggtaa aaatatgttt      780
gcggttgctg agttttggaa gaatgattta ggtgcaattg aaaactatct gcagaaaaca      840
aactggaacc attcagtctt tgatgtgccg ttacattata atctgtataa tgcatcaaaa      900
agcggaggga actatgatat gcgaaacata tttaatggaa cggttgttca acgacatcca      960
agtcatgctg taacatttgt tgataatcat gattcgcagc ctgaagaagc attagaatct     1020
tttgttgaag aatggtttaa accattagcg tatgcgctta cattaacgcg tgaacaagga     1080 taccettctg tattttacgg agattattat gggattccaa cacatggagt gccagcaatg     1140
agatcaaaaa tcgatccgat tttagaagca cgtcaaaagt atgcatacgg aaaacaaaat     1200
gattacttag accatcataa tatcattggt tggacgcgtg aaggggattc tacaaaagca     1260
aattcaggtc tagctaccat catgtctgat ggaccaggtg gaagtaagtg gatgaatgtt     1320
gggaaaaata tgctggtca agtatggagt gatattacag gaaaccgtac aggtacggtt     1380
acaatcaatg cagacggttg gggccaattc tttgtgaatg gagggtcagt ttctatttgg     1440
gtcaacaaat aa                                                        1452

<210> SEQ ID NO 12
<211> LENGTH: 1449
<212> TYPE: DNA
<213> ORGANISM: Artificial
<220> FEATURE:
<223> OTHER INFORMATION: Coding sequence for Amy707 variant

<400> SEQUENCE: 12
gcaacagtga ataacgggac attaatgcaa tactttgaat ggtatctacc taatgacgga       60
caacattgga atcgattaaa ctctgatgcg agtaaccttta aaagcaaagg gattacagcg      120
gtgtggattc ctccagcata taagggcaca acgcaaaatg acgtaggata cggagcctat      180
gacctgtatg atctgggaga atttaatcaa aaaggtaccg tccgtacaaa atatggaaca      240
cgtagtcagt tacaagctgc ggtaaccctc cttaaaaaata atggaattca agtatatggt      300
gacgcggtta tgaatcacaa aggtggcgca gacgctactg aaatggtaag ggccgttgaa      360
gtgaatccct ctaaccgtaa ccaagaaaca tctggtgaat ataatattca gcttggact      420 ggatttaatt tccagggcg aggaaatact cattctagct ttaaatggag atggtatcat      480
tttgatggtg tggattggga tcagtcacgt agactgaaca atcgcatcta taaatttgat      540
ggcaaagctt gggattggcc agttagttct gaaaatggta attatgatta tttgatgtac      600
gctgatttag attttgatca cccagatgta gtaaatgaaa tgaaggaatg gggtgtttgg      660
tacgcaaaca cattaggact cgatggattt agaatagatg cggttaaaca tataaagtat      720
agctttacgc gcgattggat taatcacgtt agaagtgcaa caggtaaaaa atatgtttgcg      780 gttgctgagt tttggaagaa tgatttaggt gcaattgaaa ctatctgca gaaacaaac      840 tggaaccatt cagtctttga tgtgccgtta cattataatc tgtataatgc atcaaaaagc      900
```

```
ggagggaact atgatatgcg aaacatattt aatggaacgg ttgttcaacg acatccaagt     960
catgctgtaa catttgttga taatcatgat tcgcagcctg aagaagcatt agaatctttt    1020
gttgaagaat ggtttaaacc attagcgtat gcgcttacat taacgcgtga acaaggatac    1080
ccttctgtat tttacggaga ttattatggg attccaacac atggagtgcc agcaatgaga    1140
tcaaaaatcg atccgatttt agaagcacgt caaaagtatg catacggaaa acaaaatgat    1200
tacttagacc atcataatat cattggttgg acgcgtgaag ggaatacagc acaccccaat    1260
tcaggtctag ctaccatcat gtctgatgga ccaggtggaa gtaagtggat gtttgttggg    1320
cgtaataagg ctggtcaagt atggagtgat attacaggaa accgtacagg tacggttaca    1380
atcaatgcag acggttgggg caatttctct gtgaatggag ggtcagtttc tatttgggtc    1440
aacaaataa                                                            1449
```